(12) United States Patent
Kapatoes

(10) Patent No.: US 12,282,125 B2
(45) Date of Patent: Apr. 22, 2025

(54) SCINTILLATOR-BASED RADIATION THERAPY QUALITY ASSURANCE

(71) Applicant: Sun Nuclear Corporation, Melbourne, FL (US)

(72) Inventor: Jeffrey M. Kapatoes, Melbourne, FL (US)

(73) Assignee: Sun Nuclear Corporation, Melbourne, FL (US)

( * ) Notice: Subject to any disclaimer, the term of this patent is extended or adjusted under 35 U.S.C. 154(b) by 267 days.

(21) Appl. No.: 17/831,260

(22) Filed: Jun. 2, 2022

(65) Prior Publication Data

US 2022/0299661 A1 Sep. 22, 2022

Related U.S. Application Data

(63) Continuation of application No. 16/925,205, filed on Jul. 9, 2020, now Pat. No. 11,378,700.

(Continued)

(51) Int. Cl.
*G01T 1/20* (2006.01)
*A61B 6/00* (2024.01)
(Continued)

(52) U.S. Cl.
CPC ............ *G01T 1/2002* (2013.01); *A61N 5/103* (2013.01); *A61N 5/1049* (2013.01);
(Continued)

(58) Field of Classification Search
CPC ... G01T 1/2002; G01T 1/2006; G01T 1/2978; A61B 6/482
See application file for complete search history.

(56) References Cited

U.S. PATENT DOCUMENTS 759,608 A 5/1904 Harper
1,239,145 A 9/1917 Wantz
(Continued)

FOREIGN PATENT DOCUMENTS

CA 2718408 9/2009
DE 102009039345 A1 3/2011
(Continued)

OTHER PUBLICATIONS

Albers et al., CRC HAndbook of Chemistry and Physics, 87th Ed., Edited by R.C. Weast CRC, Cleveland, 1976. pp. F-11, D-171, E-6. (4 pages).

(Continued)

*Primary Examiner* — Blake C Riddick
(74) *Attorney, Agent, or Firm* — Pillsbury Winthrop Shaw Pittman LLP

(57) ABSTRACT

Systems, methods, and computer software are disclosed for determining a shape of a radiation field generated by a radiation delivery system through the use of a scintillator and a camera that is configured to acquire images of light emitted by the scintillator during delivery of a radiation beam. A support structure may be mounted to the radiation delivery system and the scintillator and camera may be fixed to the support structure such that the scintillator is not perpendicular to the axis of the radiation beam. An edge detection algorithm may be applied to radiation patterns present in the camera images in order to determine the location of an edge of a leaf of a multi-leaf collimator.

21 Claims, 12 Drawing Sheets

Related U.S. Application Data

(60) Provisional application No. 62/872,646, filed on Jul. 10, 2019.

(51) Int. Cl.
*A61N 5/10* (2006.01)
*G01T 1/29* (2006.01)
*G06T 7/00* (2017.01)
*G06T 7/13* (2017.01)
*G06T 7/60* (2017.01)

(52) U.S. Cl.
CPC .......... *A61N 5/1067* (2013.01); *G01T 1/2006* (2013.01); *G01T 1/2978* (2013.01); *G06T 7/0012* (2013.01); *G06T 7/13* (2017.01); *G06T 7/60* (2013.01); *A61B 6/482* (2013.01); *A61N 5/1065* (2013.01); *G06T 2207/10116* (2013.01)

(56) References Cited

U.S. PATENT DOCUMENTS

| | | |
|---|---|---|
| 2,818,510 A | 12/1957 | Verse |
| 3,033,985 A | 5/1962 | Petree |
| 3,267,728 A | 8/1966 | Solomons |
| 3,327,213 A | 6/1967 | Wald, Jr. |
| 3,394,258 A | 7/1968 | Schleiger |
| 3,433,953 A | 3/1969 | Sweet |
| 3,665,762 A | 5/1972 | Domen |
| 3,783,251 A | 1/1974 | Pavkovich |
| 3,790,794 A | 2/1974 | Murray |
| 3,978,336 A | 8/1976 | Roux |
| 3,980,885 A | 9/1976 | Steward |
| 4,058,832 A | 11/1977 | Vagi |
| 4,063,097 A | 12/1977 | Barrett |
| 4,107,531 A | 8/1978 | Garratt |
| 4,157,472 A | 6/1979 | Barrett |
| 4,312,224 A | 1/1982 | Domen |
| 4,450,440 A | 5/1984 | White |
| 4,455,609 A | 6/1984 | Inamura |
| 4,613,754 A | 9/1986 | Vinegar |
| 4,729,099 A | 3/1988 | Iverson |
| 4,765,749 A | 8/1988 | Bourgade |
| 4,777,442 A | 10/1988 | Rosenthal |
| 4,871,914 A | 10/1989 | Simon |
| 4,887,287 A | 12/1989 | Cobben |
| 5,059,801 A | 10/1991 | Burgess |
| 5,099,505 A | 3/1992 | Seppi |
| 5,160,337 A | 11/1992 | Cosman |
| 5,262,649 A | 11/1993 | Antonuk |
| 5,388,142 A | 2/1995 | Morris |
| 5,394,452 A | 2/1995 | Swerdloff |
| 5,596,653 A | 1/1997 | Kurokawa |
| 5,602,892 A | 2/1997 | Llacer |
| 5,621,214 A | 4/1997 | Sofield |
| 5,622,187 A | 4/1997 | Carol |
| 5,627,367 A | 5/1997 | Sofield |
| 5,635,709 A | 6/1997 | Sliski |
| 5,640,436 A | 6/1997 | Kawai |
| 5,652,430 A | 7/1997 | Lee |
| 5,661,310 A | 8/1997 | Jones |
| 5,704,890 A | 1/1998 | Bliss |
| 5,712,482 A | 1/1998 | Gaiser |
| 5,873,826 A | 2/1999 | Gono |
| 5,988,875 A | 11/1999 | Gershfeld |
| 6,038,283 A | 3/2000 | Carol |
| 6,125,335 A | 9/2000 | Simon |
| 6,131,690 A | 10/2000 | Galando |
| 6,148,272 A | 11/2000 | Bergstrom |
| 6,175,761 B1 | 1/2001 | Frandsen |
| 6,207,952 B1 | 3/2001 | Kan |
| 6,257,552 B1 | 7/2001 | Crow |
| 6,261,219 B1 | 7/2001 | Meloul |
| 6,301,329 B1 | 10/2001 | Surridge |
| 6,322,249 B1 | 11/2001 | Wofford |
| 6,345,114 B1 | 2/2002 | Mackie |
| 6,364,529 B1 | 4/2002 | Dawson |
| 6,398,710 B1 | 6/2002 | Ishikawa |
| 6,466,644 B1 | 10/2002 | Hughes |
| 6,516,046 B1 | 2/2003 | Froehlich |
| 6,535,574 B1 | 3/2003 | Collins |
| 6,535,756 B1 | 3/2003 | Simon |
| 6,552,347 B1 | 4/2003 | Dimcovski |
| 6,560,311 B1 | 5/2003 | Shepard |
| 6,594,336 B2 | 7/2003 | Nishizawa |
| 6,609,626 B2 | 8/2003 | Young |
| 6,609,826 B1 | 8/2003 | Fujii |
| 6,626,569 B2 | 9/2003 | Reinstein |
| 6,636,622 B2 | 10/2003 | Mackie |
| 6,648,503 B2 | 11/2003 | Tanaka |
| 6,712,508 B2 | 3/2004 | Nilsson |
| 6,788,759 B2 | 9/2004 | Op De Beek |
| 6,799,068 B1 | 9/2004 | Hartmann |
| 6,810,107 B2 | 10/2004 | Steinberg |
| 6,810,108 B2 | 10/2004 | Clark |
| 6,833,707 B1 | 12/2004 | Dahn |
| 6,839,404 B2 | 1/2005 | Clark |
| 6,853,702 B2 | 2/2005 | Renner |
| 6,888,919 B2 | 5/2005 | Graf |
| 6,904,119 B2 | 6/2005 | Oikawa |
| 6,904,125 B2 | 6/2005 | Van Dyk |
| 6,904,162 B2 | 6/2005 | Robar |
| 6,974,254 B2 | 12/2005 | Paliwal |
| 6,990,368 B2 | 1/2006 | Simon |
| 6,992,309 B1 | 1/2006 | Petry |
| 7,016,454 B2 | 3/2006 | Warnberg |
| 7,065,812 B2 | 6/2006 | Newkirk |
| 7,076,023 B2 | 7/2006 | Ghelmansarai |
| 7,098,463 B2 | 8/2006 | Adamovics |
| 7,116,749 B2 | 10/2006 | Besson |
| 7,125,163 B2 | 10/2006 | Eigler |
| 7,127,028 B2 | 10/2006 | Sendai |
| 7,127,030 B2 | 10/2006 | Tamegai |
| 7,142,634 B2 | 11/2006 | Engler |
| 7,193,220 B1 | 3/2007 | Navarro |
| 7,221,733 B1 | 5/2007 | Takai |
| 7,233,688 B2 | 6/2007 | Ritt |
| 7,234,355 B2 | 6/2007 | Dewangan |
| 7,298,820 B2 | 11/2007 | Nelson |
| 7,339,159 B2 | 3/2008 | Juh |
| 7,349,523 B2 | 3/2008 | Jenkins |
| 7,352,840 B1 | 4/2008 | Nagarkar |
| 7,371,007 B2 | 5/2008 | Nilsson |
| 7,386,089 B2 | 6/2008 | Endo |
| 7,420,160 B2 | 9/2008 | Delaperriere |
| 7,453,976 B1 | 11/2008 | Yin |
| 7,455,449 B2 | 11/2008 | Nishimura |
| 7,471,765 B2 | 12/2008 | Jaffray |
| 7,515,681 B2 | 4/2009 | Ebstein |
| 7,579,608 B2 | 8/2009 | Takahashi |
| 7,605,365 B2 | 10/2009 | Chen |
| 7,636,419 B1 | 12/2009 | Nelson |
| 7,668,292 B2 | 2/2010 | Bose |
| 7,734,010 B2 | 6/2010 | Otto |
| 7,750,311 B2 | 7/2010 | Daghighian |
| 7,766,903 B2 | 8/2010 | Blumenkranz |
| 7,773,723 B2 | 8/2010 | Nord |
| 7,778,383 B2 | 8/2010 | Koehler |
| 7,778,392 B1 | 8/2010 | Berman |
| 7,778,680 B2 | 8/2010 | Goode, Jr. |
| 7,782,998 B2 | 8/2010 | Langan |
| 7,945,022 B2 | 5/2011 | Nelms |
| 8,044,359 B2 | 10/2011 | Simon |
| 8,093,549 B2 | 1/2012 | Navarro |
| 8,130,905 B1 | 3/2012 | Nelms |
| 8,136,773 B2 | 3/2012 | Schmutzer |
| 8,147,139 B2 | 4/2012 | Papaioannou |
| 8,218,718 B2 | 7/2012 | Van Herk |
| 8,235,530 B2 | 8/2012 | Maad |
| 8,242,458 B2 | 8/2012 | Rinecker |
| 8,321,179 B2 | 11/2012 | Simon |
| 8,325,878 B2 | 12/2012 | McNutt |
| 8,430,564 B2 | 4/2013 | Simmons |
| 8,457,713 B2 | 6/2013 | Kagermeier |
| 8,474,794 B2 | 7/2013 | Liljedahl |

(56) References Cited

U.S. PATENT DOCUMENTS

| | | |
|---|---|---|
| 8,536,547 B2 | 9/2013 | Maurer |
| 8,541,756 B1 | 9/2013 | Treas |
| 8,605,857 B1 | 12/2013 | Renner |
| 8,632,448 B1 | 1/2014 | Schulte |
| 8,726,814 B1 | 5/2014 | Matteo |
| 8,794,899 B2 | 8/2014 | Cozza |
| 8,833,709 B2 | 9/2014 | Weng |
| 8,840,304 B2 | 9/2014 | Perez Zarate |
| 8,840,340 B2 | 9/2014 | Eisenhower |
| 8,874,385 B2 | 10/2014 | Takayanagi |
| 8,927,921 B1 | 1/2015 | Nelms |
| 9,050,460 B2 | 6/2015 | Hildreth |
| 9,097,384 B1 | 8/2015 | Simon |
| 9,310,263 B2 | 4/2016 | Thoen |
| 9,463,336 B2 | 10/2016 | Nelms |
| 9,480,861 B2 | 11/2016 | Kapatoes |
| 9,561,388 B2 | 2/2017 | Hildreth |
| 9,586,060 B2 | 3/2017 | Seuntjens |
| 9,750,955 B2 | 9/2017 | McNutt |
| 9,895,557 B2 | 2/2018 | Seuntjens |
| 10,099,067 B2 | 10/2018 | Kapatoes |
| 10,413,754 B2 | 9/2019 | Seuntjens |
| 10,755,823 B2 | 8/2020 | Carette |
| 2001/0042841 A1 | 11/2001 | Lyons |
| 2002/0077545 A1 | 6/2002 | Takahashi |
| 2002/0080912 A1 | 6/2002 | Mackie |
| 2003/0043879 A1 | 3/2003 | Tanaka |
| 2003/0043960 A1 | 3/2003 | Op De Beek |
| 2003/0138077 A1 | 7/2003 | Lee |
| 2003/0231740 A1 | 12/2003 | Paliwal |
| 2004/0066880 A1 | 4/2004 | Oikawa |
| 2004/0068182 A1 | 4/2004 | Misra |
| 2004/0096033 A1 | 5/2004 | Seppi |
| 2004/0113094 A1 | 6/2004 | Lyons |
| 2004/0120560 A1 | 6/2004 | Robar |
| 2004/0129888 A1 | 7/2004 | Kannan |
| 2004/0158145 A1 | 8/2004 | Ghelmansarai |
| 2004/0211917 A1 | 10/2004 | Adamovics |
| 2004/0228435 A1 | 11/2004 | Russell |
| 2004/0251419 A1 | 12/2004 | Nelson |
| 2005/0013406 A1 | 1/2005 | Dyk |
| 2005/0077459 A1 | 4/2005 | Engler |
| 2005/0111621 A1 | 5/2005 | Riker |
| 2005/0281389 A1 | 12/2005 | Kusch |
| 2006/0002519 A1 | 1/2006 | Jenkins |
| 2006/0033044 A1 | 2/2006 | Gentry |
| 2006/0184124 A1 | 8/2006 | Cowan |
| 2006/0203964 A1 | 9/2006 | Nyholm |
| 2006/0203967 A1 | 9/2006 | Nilsson |
| 2006/0266951 A1 | 11/2006 | Fritsch |
| 2007/0041497 A1 | 2/2007 | Schnarr |
| 2007/0041499 A1 | 2/2007 | Lu |
| 2007/0053492 A1 | 3/2007 | Kidani |
| 2007/0071169 A1 | 3/2007 | Yeo |
| 2007/0081629 A1 | 4/2007 | Yin |
| 2007/0086577 A1 | 4/2007 | Kobayashi |
| 2007/0172020 A1 | 7/2007 | Nambu |
| 2007/0181815 A1 | 8/2007 | Ebstein |
| 2007/0195930 A1 | 8/2007 | Kapatoes |
| 2008/0031406 A1 | 2/2008 | Yan |
| 2008/0049896 A1 | 2/2008 | Kuduvalli |
| 2008/0049898 A1 | 2/2008 | Romesberg, III |
| 2008/0091388 A1 | 4/2008 | Failla |
| 2008/0103834 A1 | 5/2008 | Reiner |
| 2008/0118137 A1 | 5/2008 | Chen |
| 2008/0146914 A1* | 6/2008 | Polzin .......... A61B 6/5247 600/420 |
| 2008/0260368 A1 | 10/2008 | Chang |
| 2008/0267352 A1* | 10/2008 | Aoi .......... H05H 7/02 378/65 |
| 2008/0292055 A1 | 11/2008 | Boone |
| 2008/0298553 A1 | 12/2008 | Takahashi |
| 2009/0003512 A1 | 1/2009 | Pouliot |
| 2009/0003528 A1 | 1/2009 | Ramraj |
| 2009/0005671 A1* | 1/2009 | Kreischer .......... A61B 6/4417 324/318 |
| 2009/0067576 A1 | 3/2009 | Maltz |
| 2009/0090870 A1 | 4/2009 | Ahnesjo |
| 2009/0175418 A1 | 7/2009 | Sakurai |
| 2009/0217999 A1 | 9/2009 | Becker |
| 2009/0227841 A1 | 9/2009 | Miyako |
| 2009/0250618 A1 | 10/2009 | Simon |
| 2009/0252292 A1 | 10/2009 | Simon |
| 2009/0326365 A1 | 12/2009 | Goldenberg |
| 2010/0008467 A1 | 1/2010 | Dussault |
| 2011/0022360 A1 | 1/2011 | Simon |
| 2011/0051893 A1 | 3/2011 | McNutt |
| 2011/0085716 A1 | 4/2011 | Christophe |
| 2011/0096906 A1 | 4/2011 | Langeveld |
| 2011/0108702 A1 | 5/2011 | Jackson |
| 2011/0158386 A1 | 6/2011 | Payne |
| 2011/0204262 A1 | 8/2011 | Pu |
| 2011/0210258 A1 | 9/2011 | Black |
| 2011/0248188 A1 | 10/2011 | Brusasco |
| 2011/0278444 A1 | 11/2011 | Navarro |
| 2011/0306864 A1 | 12/2011 | Zarate |
| 2012/0014618 A1 | 1/2012 | Sun |
| 2012/0025105 A1 | 2/2012 | Brown |
| 2012/0025826 A1 | 2/2012 | Zhou |
| 2012/0097860 A1 | 4/2012 | Oguma |
| 2012/0230462 A1 | 9/2012 | Robar |
| 2012/0292517 A1 | 11/2012 | Izaguirre |
| 2012/0305793 A1 | 12/2012 | Schiefer |
| 2012/0326057 A1 | 12/2012 | Remeijer |
| 2013/0048869 A1 | 2/2013 | Kominami |
| 2013/0048883 A1 | 2/2013 | Simon |
| 2013/0119259 A1* | 5/2013 | Martin .......... A61B 6/037 250/363.03 |
| 2013/0258105 A1 | 10/2013 | Jozsef |
| 2013/0267830 A1* | 10/2013 | Ojha .......... A61B 5/0035 600/1 |
| 2013/0287170 A1* | 10/2013 | Ebstein .......... G01N 23/04 378/62 |
| 2013/0303902 A1 | 11/2013 | Smith |
| 2014/0016754 A1 | 1/2014 | Sugiyama |
| 2014/0064445 A1 | 3/2014 | Adler |
| 2014/0073834 A1 | 3/2014 | Hildreth |
| 2014/0077098 A1 | 3/2014 | Tachikawa |
| 2014/0094642 A1 | 4/2014 | Fuji |
| 2014/0105355 A1 | 4/2014 | Toimela |
| 2014/0221816 A1* | 8/2014 | Franke .......... G01R 33/4828 600/1 |
| 2014/0237213 A1 | 8/2014 | Gill |
| 2014/0250480 A1 | 9/2014 | Koh |
| 2014/0263990 A1 | 9/2014 | Kawrykow |
| 2014/0316258 A1* | 10/2014 | Hahn .......... A61B 6/037 600/425 |
| 2015/0071408 A1* | 3/2015 | Ebstein .......... A61N 5/1075 378/65 |
| 2015/0080634 A1 | 3/2015 | Huber |
| 2015/0087879 A1 | 3/2015 | Nelms |
| 2015/0108356 A1 | 4/2015 | Seuntjens |
| 2015/0124930 A1 | 5/2015 | Verhaegen |
| 2015/0238778 A1 | 8/2015 | Hildreth |
| 2015/0283403 A1 | 10/2015 | Kapatoes |
| 2015/0309193 A1 | 10/2015 | Kozelka |
| 2015/0327825 A1 | 11/2015 | Suzuki |
| 2015/0352376 A1 | 12/2015 | Wiggers |
| 2016/0067479 A1 | 3/2016 | Marcovecchio |
| 2016/0136460 A1 | 5/2016 | Baltes |
| 2016/0166857 A1 | 6/2016 | Nelms |
| 2016/0256712 A1* | 9/2016 | Vahala .......... A61N 5/1039 |
| 2016/0287906 A1 | 10/2016 | Nord |
| 2016/0310762 A1 | 10/2016 | Ramezanzadeh Moghadam |
| 2016/0354048 A1* | 12/2016 | Lee .......... G21K 5/04 |
| 2016/0361568 A1 | 12/2016 | Chappelow |
| 2017/0021194 A1 | 1/2017 | Nelms |
| 2017/0135580 A1* | 5/2017 | Lips .......... A61B 5/0035 |
| 2017/0173367 A1 | 6/2017 | Seuntjens |
| 2017/0177812 A1 | 6/2017 | Sjölund |
| 2017/0225015 A1 | 8/2017 | Thieme |
| 2017/0274225 A1 | 9/2017 | Baecklund |
| 2018/0014798 A1 | 1/2018 | Beckman |

(56) References Cited

U.S. PATENT DOCUMENTS

| | | | |
|---|---|---|---|
| 2018/0028143 | A1 | 2/2018 | Wiggers |
| 2018/0028840 | A1 | 2/2018 | Simon |
| 2018/0043183 | A1 | 2/2018 | Sheng |
| 2018/0074143 | A1* | 3/2018 | Delso ............... G01R 33/481 |
| 2018/0140272 | A1 | 5/2018 | Ruchala |
| 2018/0185672 | A1 | 7/2018 | Ramezanzadeh Moghadam |
| 2018/0243586 | A1 | 8/2018 | Ramezanzadeh Moghadam |
| 2018/0250529 | A1 | 9/2018 | Seuntjens |
| 2018/0250531 | A1 | 9/2018 | Ansorge |
| 2018/0344274 | A1* | 12/2018 | Berr ..................... G01F 1/66 |
| 2019/0014243 | A1 | 1/2019 | Malone |
| 2019/0118002 | A1 | 4/2019 | Rosenwald |
| 2019/0298285 | A1 | 10/2019 | Rakic |
| 2020/0061389 | A1* | 2/2020 | Willcut .............. G06T 7/0016 |
| 2020/0101327 | A1 | 4/2020 | Alquist |
| 2020/0253001 | A1 | 8/2020 | Nauditt |
| 2021/0011178 | A1 | 1/2021 | Kapatoes |
| 2021/0012507 | A1 | 1/2021 | Kapatoes |
| 2021/0015441 | A1* | 1/2021 | Bourne ............... A61N 5/1075 |
| 2021/0220676 | A1* | 7/2021 | Kawrykow .......... G21K 1/046 |
| 2021/0236856 | A1 | 8/2021 | Kapatoes |

FOREIGN PATENT DOCUMENTS

| | | |
|---|---|---|
| EP | 1060726 | 12/2000 |
| EP | 1060726 B1 | 6/2004 |
| EP | 2016445 | 1/2009 |
| EP | 2078537 A1 | 7/2009 |
| EP | 2117649 A2 | 11/2009 |
| EP | 2186542 | 5/2010 |
| EP | 2400317 A1 | 12/2011 |
| EP | 2457237 | 5/2012 |
| EP | 2708919 A2 | 3/2014 |
| EP | 2865417 | 4/2015 |
| EP | 2904974 | 8/2015 |
| EP | 3074088 | 10/2016 |
| EP | 3075417 | 10/2016 |
| JP | 05154209 | 6/1993 |
| JP | 2003310590 A | 11/2003 |
| JP | 2008105882 | 5/2008 |
| JP | 2010215428 | 9/2010 |
| JP | 2010234521 | 10/2010 |
| JP | 202035449 | 3/2020 |
| WO | 2006138513 | 12/2006 |
| WO | 2008013956 | 1/2008 |
| WO | 2009114669 | 9/2009 |
| WO | 2009120494 | 10/2009 |
| WO | 2009137794 | 11/2009 |
| WO | 2011011471 | 1/2011 |
| WO | 2012053440 | 4/2012 |
| WO | 2013049839 | 4/2013 |
| WO | 2013177677 A | 12/2013 |
| WO | 2015024360 | 2/2015 |
| WO | 2015073899 | 5/2015 |
| WO | 2016172352 | 10/2016 |
| WO | 2016200463 | 12/2016 |
| WO | 2019157249 A | 8/2019 |

OTHER PUBLICATIONS

Almond et al. In "AAPM TG-51 Protocol for Clinical Reference Dosimetry of High Energy Photon and Electron Beams", Med. Phys. VI, 26, pp. 1847-1870, 1999.

Aspen Aerogels, Pyrogel.RTM. 2250 Datasheet (Aspen Aerogels, Inc., Northborough, 2010). 2 pages.

Berlyand et al., "Portable Calorimeter for Measuring Absorbed Doses of X-Rays and Electrons from Accelerators", translated from Izeritel'naya Teknika, No. 11, Nov. 1991, pp. 56-58.

Boutillon in "Gap Correction for the Calorimetric Measurement of Absorbed Dose in Graphite with a 60Co Beam", Phys. Med. Biol., vol. 34, pp. 1809-1821, 1989.

Daures et al., "New Constant-Temperature Operating Mode for Graphite Calorimeter at LNE-LNHB", Physics in Medicine and Biology, vol. 50, 2005, No. pp. 4035-4052.

Daures et al., "Small section graphite calorimeter (CR10) at LNE-LNHB for measurement in small beams for IMRT", Metrologica, (Dec. 1, 2011), XP020229547, 5 pages.

Daures et al., "Small Section Graphite Calorimeter (GR-10) at LNE-LNHB for Measurements in Small Beams for IMRT Metrologia", vol. 49, No. 5, 2012, pp. S174-S178.

Domen et al., "A Heat-loss-Compensated Calori meter: Theory, Design, and Performance", Journal of Research of the National Bureau of Standards—A. Physics and Chemistry, vol. 78A, No. 5, Sep.-Oct. 1974, pp. 595-610.

Domen, "Absorbed Dose Water Calorimeter", (Med. Phys., vol. 7, 1980, pp. 157-159).

Duane et al., "An Absorbed Dose Calorimeter for IMRT Dosimetry", Metrologia, vol. 49, No. 5, 2012, pp. S168-S173.

IAEA, TRS., "398. Absorbed Dose Determination in External Beam Radiotherapy: An International Code of Practice for Dosimetry based on Standards of Absorbed Dose to Water," Vienna International Atomic Energy Agency (2000). 242 pages.

J. Seuntjens and S. Duane, "Photon absorbed dose standards," Metrologia 46, S39-S58 (2009).

Kawrakow et al. In "The EGSnrc Code System: Monte-Carlo Simulation of Electron and Photon Transport" (Canadian National Research Center, NRC Report PIRS-701, 2006.

McEwen at al., 'A Portable Calorimeter for Measuring Absorbed Dose in the Radiotherapy Clinic', Physics in Medicine and Biology, vol. 45, No. 12, Dec. 2000, pp. 3675-3691.

McDonald et al., "Portable Tissue Equivalent Calorimeter", Medical Physics, vol. 3, 2, Mar.-Apr. 1976, pp. 80-86.

McEwen et al., "Portable Graphite Calorimeter for Measuring Absorbed Dose in the Radiotherapy Clinic", Standards and Codes of Practice in Medical Radiation Dosimetry, IAEA-CN-96-9P,2002, pp. 115-121.

Miller, "Polystyrene Calorimeter for Electron Beam Dose Measurements", Radiation Physics Chemistry vol. 46, No. 4-6, Aug. 1995, pp. 1243-1246.

Myers et al., "Precision Adiabatic Gamma-Ray Calorimeter using Thermistor Thermometry", Review of Scientific Instruments, vol. 32, No. 9, Sep. 1961, pp. 1013-1015.

Nutbrown et. "Evaluation of Factors to Convert Absorbed Dose Calibrations in Graphite to Water for Mega-Voltage Photon Beams" (UK National Pysical Laboratory, NPL Report CIRM 37, 2000. 45 pages.

Ostrowsky et al., "The Construction of the Graphite Calorimeter GR9 at LNE-LNHB (Geometrical and technical considerations)", Report CEA-R-6184, 2008, 52 pages.

Owen et al "Correction for the Effect of the Gaps around the Core of an Absorbed Dose Graphite Calorimeter in High Energy Photon Radiation" (Phys. Med. Biol., vol. 36, pp. 1699-1704, 1991.

Palmans et al., "A Small-Body Portable Graphite Calorimeter for Dosimetry in Low-Energy Clinical Proton Beams", Physics in Medicine and Biology, vol. 49, No. 16, Aug. 2004, pp. 3737-3749.

Petree et al., "A Comparison of Absorbed Dose Determinations in Graphite by Cavity Ionization Measurements and by Calorimetry", Journal of Research of the National Bureau of Standards—C. Engineering and Instrumentation. vol. 71 C, No. 1, Jan.-Mar. 1967, pp. 19-27.

Picard et al., "Construction of an Absorbed-Dose Graphite Calorimeter", Report BIPM-09/01' May 2009, 12 pages.

R. Alfonso et al., 'A new formalism for reference dosimetry of small and nonstandard fields,' Med. Phys. 35, 5179-5186 (2008).

Renaud et al., "Development of a graphite probe calorimeter for absolute clinical dosimetry", Med. Phvs., (Jan. 9, 2013), vol. 40, No. 2, p. 020701, XP012170941, 6 pages.

Rogers, "The physics of AAPM's TG-51 protocol," in Clinical Dosimetry Measurements in Radiotherapy, Medical Physics Monograph No. 34, edited by D. W. O. Rogers and J. E. Cygler (Medical Physics Publishing, Madison, WI, 2009), pp. 239-298.

Ross et al. In "Water Calorimetry for Radiation Dosimetry" (Phys. Med. Biol., 1996, vol. 41, pp. 1-29).

(56) References Cited

OTHER PUBLICATIONS

S. Picard, D. T. Burns, and P. Roger, "Determination of the specific heat capacity of a graphite sample using absolute and differential methods," Metrologia 44, 294-302 (2007).
Sander et al., "NPL's new absorbed dose standard for the calibration of HDR 192Ir brachytherapy sources," Metrologia 49, S184-S188 (2012).
Seuntjens et al., Review of Calorimeter Based Absorbed Dose to Water Standards, Standards and Codes of Practice in Medical Radiation Dosimetry, IAEA-CN-96-3, 2002 p. 37-66.
Stewart in "The Development of New Devices for Accurate Radiation Dose Measurement: A garded Liquid Ionization Chamber and an Electron Sealed Water Calorimeter" Ph. D. Dissertation McGill University, 2007.
Sundara et al., "Graphite Calorimeter in Water and Calibration of Ionization Chambers in Dose to Water for 60Co Gamma Radiation", Medical Physics, vol. 7, No. 3, May-Jun. 1980, pp. 196-201.
Witzani et al., "A Graphite Absorbed-Dose Calorimeter in the Quasi-Isothermal Mode of Operation", Metrologia, vol. 20, No. 3, 1984, pp. 73-79.
Y. Morishita et al., "A standard for absorbed dose rate to water in a 60Co field using a graphite calorimeter at the national metrology institute of Japan," Radiat. Prot. Dosim. 1-9 (2012) (published E-first Sep. 5, 2012).
Brusasco, C, et al. 'A Dosimetry System for Fast Measurement of 3D Depth-dose Profiles in Charged-particle Tumor Therapy with Scanning Techniques.' Nuclear Instruments & Methods In Physics Research, Section—B: Beam Interactions With Materials And Atom 168.4 (2000): 578-92.
PCT App. No. PCT/US2015/024360; International Search Report and Written Opinion mailed Oct. 8, 2015; 13 page.
PCT App. No. PCT/US2015/024360; International Preliminary Report on Patentability Chapter I mailed Oct. 4, 2016; 9 pages.
Nelms, Benjamin. "Variation in External Beam Treatment, Plan Quality: An Inter-institutional Study of Planners and Planning Systems." Practical Radiation Oncology 2.4 (2012): 296-305.
PCT App. No. PCT/US2014/065808; International Search Report and Written Opinion mailed May 21, 2015; 9 pages.
PCT App. No. PCT/US2014/065808; International Preliminary Report on Patentability Chapter I mailed May 17, 2016; 7 pages.
Mackie et al., "Photon Beam Dose Computations", Proceedings of the 1996 AAPM Summer School, 1996. 36 pages.
PCT App. No. PCT/US2012/058345; International Search Report mailed Apr. 17, 2013; 3 pages.
Ahnesjo et al., "Calculation and Application of Point Spread Functions for Treatment Planning with High Energy Photon Beams", Acta. Oncol., 26, 49-56, 1987.
PCT App. No. PCT/US2012/058345; International Preliminary Report on Patentability Chapter I mailed Apr. 1, 2014; 5 pages.
PCT App. No. PCT/US2012/058345; International Written Opinion of the International Search Authority mailed Mar. 29, 2014; 4 pages.
Ahnesjo et al., "Dose calculations for external photon beams in radiotherapy", Phys. Med. Biol. 44, R99-R155 1999.
Ahnesjo, "Collapsed Cone Convolution of Radiant Energy for Photon Dose Calculation in Heterogeneous Media", Med. Phys. 16, 577-92, 1989.
Amanatides et al., "A Fast Voxel Traversal Algorithm for Ray Tracing", Eurographics '87, Conference Proceedings, 1987, 10 pages.
International Search Report and Written Opinion mailed Sep. 1, 2023, PCT Application No. PCT/iB/2023/055991.
Jaccard, Maud, et al. "High dose-per-pulse electron beam dosimetry: commissioning of the Oriatron eRT6 prototype linear accelerator for preclinical use." Medical physics 45.2 (2018): 863-874. (Year: 2018).
Barthe, Jean. "Electronic dosimeters based on solid state detectors." Nuclear Instruments and Methods in Physics Research Section B: Beam Interactions with Materials and Atoms 184.1-2 (2001): 158-189. (Year: 2001).

Liu et al., "Correcting kernel tilting and hardening in convolution/superposition dose calculations for clinical devergent and polychomatic photon beams", Med. Phys. 24, 1729-1741, 1997.
Lu et al., "Accurate convolution/superposition for multi-resolution dose calculation using cumulative tabulated kernels", Phys. Med. Biol. 50, 655-680, 2005.
Mackie et al., The Use of Comp. In Rad. Ther., 107-110 1987.
Mackie et al., "Generation of Photon Energy Deposition Kernels Using the EGS Monte Carlo Code," 1988, Phys. Med. Biol. 33, pp. 1-20.
Mackie et al., "A convolution method of calculating dose for 15-MVx rays", Med. Phys. 12, 188-196, 1985.
Mohan et al., "Energy and angular distributions of photons from medical linear accelerators", Med. Phys. 12, 592-597, 1985.
Otto, "Volumetric modulated arc therapy: IMRT in a single gantry arc", Med. Phys. 35, 310-317, 2008.
Papanikolaou et al., "Investigation of the convolution method for polyenergetic spectra", Med. Phys. 20, 1327-1336, 1993.
Williams, "Pyramidal Parametrics", SIGGRAPH Comput. Graph. 17, 3, 1-11, 1983.
Yan et al., "Adaptive radiation therapy", Phys. Med. Biol. 42, 123-132, 1997.
Yu, "Intensity-modulated arc therapy with dynamic multileaf collimation: an alternative to tomotherapy", Phys. Med. Biol. 40, 1435-1449, 1995.
PCT App. No. PCT/US2009/043341; International Search Report mailed Jan. 5, 2010. 3 pages.
PCT App. No. PCT/US2009/043341; Written Opinion of the International Search Authority mailed Nov. 8, 2010. 3 pages.
PCT App. No. PCT/US2009/043341; International Preliminary Report on Patentability Chapter I mailed Nov. 9, 2010. 4 pages.
PCT App. No. PCT/US2012/053440; International Search Report and Written Opinion mailed Mar. 26, 2014; 3 pages.
"Waterphantom Dosimetry"; Medical Physics, vol. 3, May/Jun. 1976; pp. 189.
Indra J. Das, Chee-Wai Cheng, Ronald J. Watt, Anders Ahnesjo, John Gibbons, X. Allen Li, Jessica Lowenstien, Raj K. Mitra, William E. Simon, Timothy C. Zhu; Accelerator Beam Data Commissioning Equiptment and Procedures; Report of the TG-106 of the Therapy Physics Committee of the AAPM; Med. Phys. 35(9), Sep. 2008; pp. 4186-4215.
PCT App. No. PCT/US2010/042680; International Search Report mailed Jan. 27, 2011; 2 pages.
PCT App. No. PCT/US2010/042680; International Written Opinion mailed Jan. 23, 2012; 8 pages.
PCT App. No. PCT/US2010/042680; International Preliminary Report on Patentability Chapter I mailed Jan. 24, 2012; 9 pages.
EP2457237 Supplemental European Search Report and Written Opinion mailed Mar. 8, 2017; 10 pages.
PCT App. No. PCT/US2009/036775; International Search Report mailed Nov. 12, 2009; 2 pages.
PCT App. No. PCT/US2009/036775; International Preliminary Report on Patentability Chapter II and Written Opinion mailed Sep. 12, 2010; 12 pages.
EP2277353 Search Report mailed Jul. 21, 2017; 10 pages.
Benedick Fraass; "Quality Assurance for Clinical Radiotherapy Treatment Planning," Med Phys., 25(10), Oct. 1998; pp. 1773-1829.
G.J. Kutcher; "Comprehensive AQ for Radiation Oncology Report;" AAPM Radiation Therapy Committee Task Group 40; Med. Phys., 21; Apr. 1994; pp. 581-618.
MapCheck and EPIDose; www.sunnuclear.com; manufactured by Sun Nuclear Corp.; Melbourne, FL; 2010, 8 pages.
MapCALC; www.sunnuclear.com; manufactured by Sun Nuclear Corp.; Melbourne, FL; 2009, 2 pages.
Joseph O. Deasy; "A Computational Environment for Radiotherapy Research," Med. Phys. 30, (5), May 2003; pp. 979-985.
Robert M. Eisberg; "Fundamentals of Modern Physics," Chapter 9—Perturbation Theory; John Wiley & Sons; 1967; pp. 268-272.
Cyberknife; Cyberknife Systems; "The Standard of Radiosurgery", by Accuracy, Sunnyvale, CA; 2009; pp. 1-6.
"Hi-Art"; www.tomotherapy.com; TomoTherapy, Madison, WI; 2007; pp. 1-8.

(56) References Cited

OTHER PUBLICATIONS

"Rapid Arc"; Varian Medical Systems, Inc., Palo Alto, CA; www.varian.com; 2007; pp. 1-8.
"VMAT"; Elekta, Ltd., Crawley UK; Document No. 4513 3710770; Oct. 8, 2008, 8 pages.
D.W.O. Rogers; "Montey Carlo Techniques in Radiotherapy," Physics in Canada, Medical Physics Special Issue, v. 58 #2; 2002; pp. 63-70.
T.R. McNutt, T.R. Mackie, P.J. Reckwerdt, B.R. Paliwal; "Analysis and Convergence of the Iterative Convolution/Superposition Dose Reconstruction Technique,"; Med. Phys. 24(9) Sep. 1997; pp. 1465-1476.
Mathilda Van Zijtveld, Maaretn L.P. Dirkxa, Hans C.J. De Boera, and Ben J.M. Heijmen; "3D Dose Reconstruction for Clinical Evaluation of IMRT Pretreatment Verification with an EPID." Radiotherapy and Oncology, 82(2); Feb. 2007; pp. 201-201.
PCT App. No. PCT/US2009/036917; International Search Report mailed Sep. 17, 2009. 2 pages.
PCT App. No. PCT/US2009/036917; Written Opinion mailed Sep. 12, 2010; 4 pages.
PCT App. No. PCT/US2009/036917; International Preliminary Report on Chapter II Patentability mailed Mar. 15, 2011. 3 pages.
PCT/US2017/044472; International Search Report and Written Opinion of the International Searching Authority, or the Declaration mailed Oct. 13, 2017; 12 pages.
PCT App. No. PCT/US2012/053440; International Preliminary Report on Patentability Chapter I mailed Mar. 3, 2015; 8 pages.
PCT App. No. PCT/US2016/028664; International Preliminary Report on Patentability mailed Nov. 2, 2017; 5 pages.
PCT App. No. PCT/US2017/062608; International Search Report and Written Opinion mailed Feb. 22, 2018; 11 pages.
McEwen et al.; "A portable calorimeter for measuring absorbed dose in radiotherapy clinic"; Dec. 2000; Phys. Med. Biol., vol. 45; pp. 3675-3691.
McDermott et al.; "Replacing Pretreatment Verification with In Vivo EPID Dosimetry for Prostate IMRT"; International Journal of Radiation: Oncology Biology Physics, Pergamon Press, USA, vol. 67, No. 5, Mar. 28, 2007, pp. 1568-1577, XP022101268, ISSN: 0360-3016, DOI: 10.1016/J.IJROBP.2006.11.047.
Nelms, Benjamin et al.; "Evalution of a Fast Method of EPID-based Dosimetry for Intensity-modulated Radiation Therapy"; Journal of Applied Clinical Medical Physics, Jan. 1, 2010, pp. 140-157, XP055476020.
PCT App. No. PCT/US2018/020320; International Search Report and Written Opinion mailed Jul. 24, 2018; 18 pages.
Linacre, J.K. , "Harwell Graphite Calorimeter", IAEA, vol. 47, 1970 (pp. 46-54.).
PCT App. No. PCT/US2018/020320; International Preliminary Report on Patentability Chapter I mailed Sep. 12, 2019. pp. 1-11.
PCT Appl. No. PCT/US2018/056568; International Preliminary Report on Patentability, mailed Apr. 30, 2020. 8 pages.
International Search Report and Written Opinion mailed Oct. 2, 2020, PCT Application No. PCT/US2020/041458.
International Search Report and Written Opinion mailed Nov. 24, 2021, PCT Application No. PCT/IB2021/057573.

\* cited by examiner

SCINTILLATOR-BASED RADIATION THERAPY QUALITY ASSURANCE

RELATED APPLICATION(S)

This application is a continuation of and claims priority to and the benefit of U.S. patent application Ser. No. 16/925,205, filed Jul. 9, 2020, titled "Scintillator-Based Radiation Therapy Quality Assurance," which claims priority to and benefit of U.S. Provisional Application No. 62/872,646, filed Jul. 10, 2019, titled "Scintillator-Based Radiation Therapy Quality Assurance," which is hereby incorporated by reference.

DESCRIPTION OF THE RELATED ART

Radiation therapy can be utilized in the treatment of diseases, for example, by delivering a dose of radiation to kill or to inhibit growth of a cancerous tumor. Devices to deliver radiation therapy can include, for example, radio-isotopes, heavy ion accelerators and linear accelerators that generate a photon beam directed at a tumor site. To irradiate a tumor while minimizing exposure to nearby healthy tissues, a radiation beam can be shaped by a collimating device, for example, a multileaf collimator (MLC). Multi-leaf collimators include a number of movable leaves that can be positioned to create a shaped aperture (e.g., shaped the same as the tumor, from the vantage point of the radiation beam).

Radiation therapy quality assurance can be performed to verify the proper operation of one or more components of a radiation therapy delivery system, for example, verifying the positioning of MLC leaves. In certain circumstances, radiation detectors such as scintillators may be used in performing such quality assurance. Scintillators emit light in response to being struck by radiation and the emitted light can be detected and analyzed to assist in determining whether radiation has been delivered properly.

SUMMARY

Systems, computer program products, and methods are disclosed for determining a shape of a radiation field generated by a radiation delivery system that includes a radiation source configured to deliver a radiation beam. An implementation of the system that determines the shape of the radiation field includes a scintillator and a camera configured to acquire images of light emitted by the scintillator during delivery of the radiation beam. The system also includes a support structure configured to be mounted to the radiation delivery system. The scintillator and the camera are fixed to the support structure such that when the support structure is mounted to the radiation delivery system, the scintillator is not perpendicular to an axis of the radiation beam.

In some implementations, the system can be configured to be located between the radiation source and a patient couch.

In other implementations, the scintillator can include a planar sheet of scintillating material. The scintillator can be transparent, allowing formation of a pattern at a target location corresponding to the shape of a collimator aperture when a light source shines light through the collimator aperture onto the scintillator.

In yet other implementations the scintillator and the camera can be fixed to the support structure in a manner that sets a specific desired geometric relationship between the scintillator and the camera. For example, the scintillator can be at an angle of between 80 to 89 degrees or between 91 and 110 degrees relative to the axis of the radiation beam when the support structure is mounted to the radiation delivery system. Also, the support structure can be configured to allow mounting in an accessory tray disposed between the radiation source and a patient couch.

In another implementation, the system includes a scintillator mounted to the radiation delivery system such that the scintillator substantially follows a contour of a bore of the radiation delivery system. The system includes cameras configured to acquire images of light emitted by the scintillator during delivery of the radiation beam. The cameras are configured to be mounted an angle of greater than 0 and less than 10 degrees relative to the scintillator.

In some implementations, the bore can be part of an MRI-guided radiotherapy system. The scintillator can be a curved sheet of scintillating material or planar sheets of scintillating material. At least a portion of the scintillator can remain perpendicular to the axis of the radiation beam when the radiation source is controlled to move around the bore.

Any of the disclosed systems can also include software that performs various operations. Such operations can include applying an edge detection algorithm to a radiation pattern present in the images. The edge detection algorithm can determine an edge of the radiation pattern corresponding to a leaf of a multi-leaf collimator. A leaf position can be determined based on a location of the determined edge.

In some implementations, the operations can include comparing the leaf position during delivery of the radiation beam with a planned leaf position, for example when utilized in radiation therapy quality assurance. A fluence map can also be calculated based at least on the leaf position and beam output data obtained from the radiation therapy system and a dose can be calculated at a target location based at least on the fluence map and a patient image obtained from an imaging system.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or across multiple computing systems. Such multiple computing systems can be connected and can exchange data and/or commands or other instructions or the like via one or more connections, including but not limited to a connection over a network (e.g., the internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

Radiation therapy quality assurance is a field that includes, among other things, determining whether a radiation delivery system is functioning properly and providing the prescribed radiation dose to a patient as detailed in a radiation therapy treatment plan. While many radiation delivery systems include their own functionality for displaying output and diagnostic metrics, radiation therapy quality assurance products can obtain independent measurements of what the radiation delivery system is providing.

As used herein, the term "radiation delivery system" can include various components needed to generate, direct and control a radiation therapy beam. For example, a radiation therapy system can include a radiation source (e.g. a linear accelerator, particle beam source, etc.), a gantry (fixed or rotating), a collimator (to shape the radiation reaching the patient), imaging equipment (to image prior to or during therapy), and the like.

As part of quality assurance, the operation of various components of the radiation delivery system can be independently assessed. Examples of such operations can include, for example, verifying the output of the radiation source, the position of a rotating gantry, the configuration of a multileaf collimator (e.g., determining its leaf positions), etc. The present disclosure describes, among other things, systems, software, and methods for determining collimator configurations based on the analysis of radiation patterns that emerge after a radiation beam passes through the collimator.

Figure 1A:
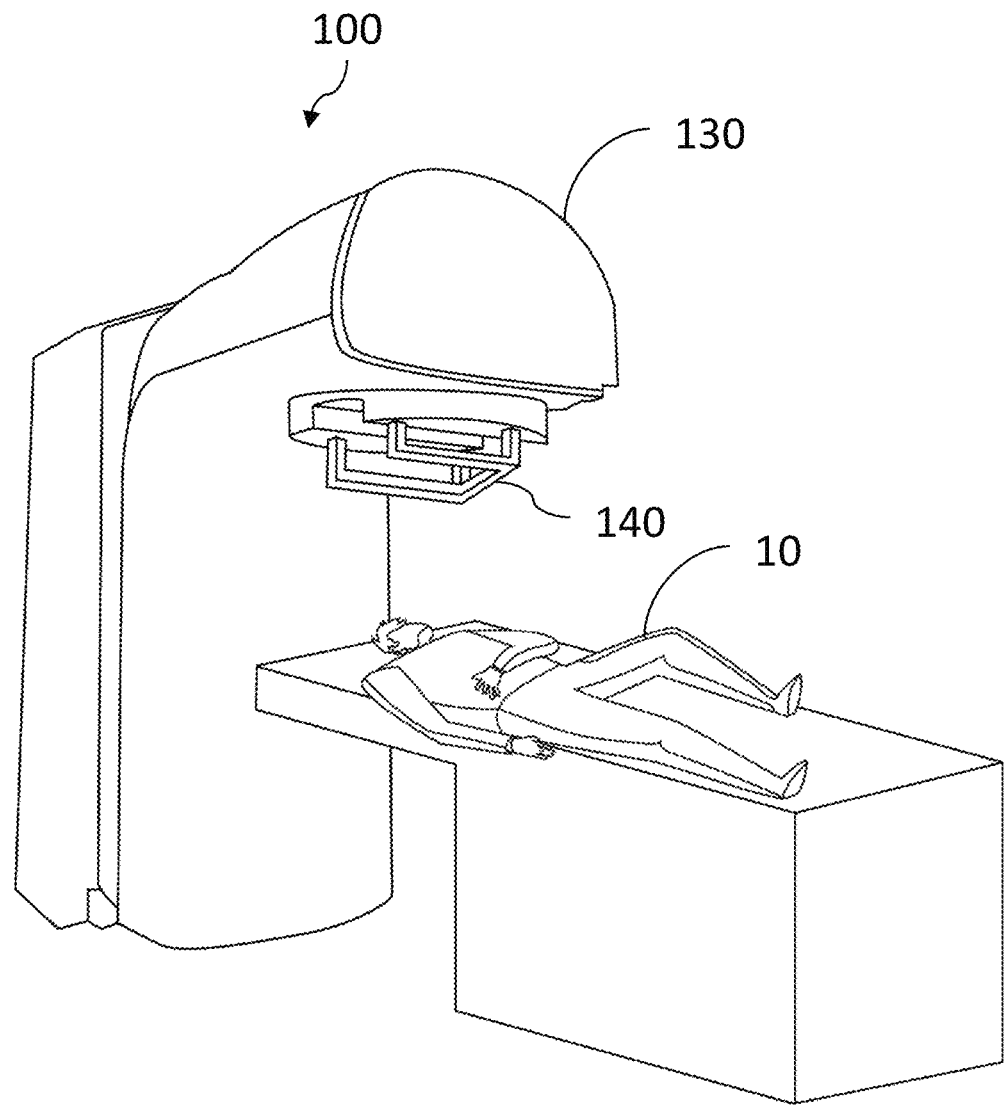
FIG. 1A is a diagram illustrating a perspective view of a simplified exemplary radiation delivery system in accordance with certain aspects of the present disclosure.
Figure 1B:
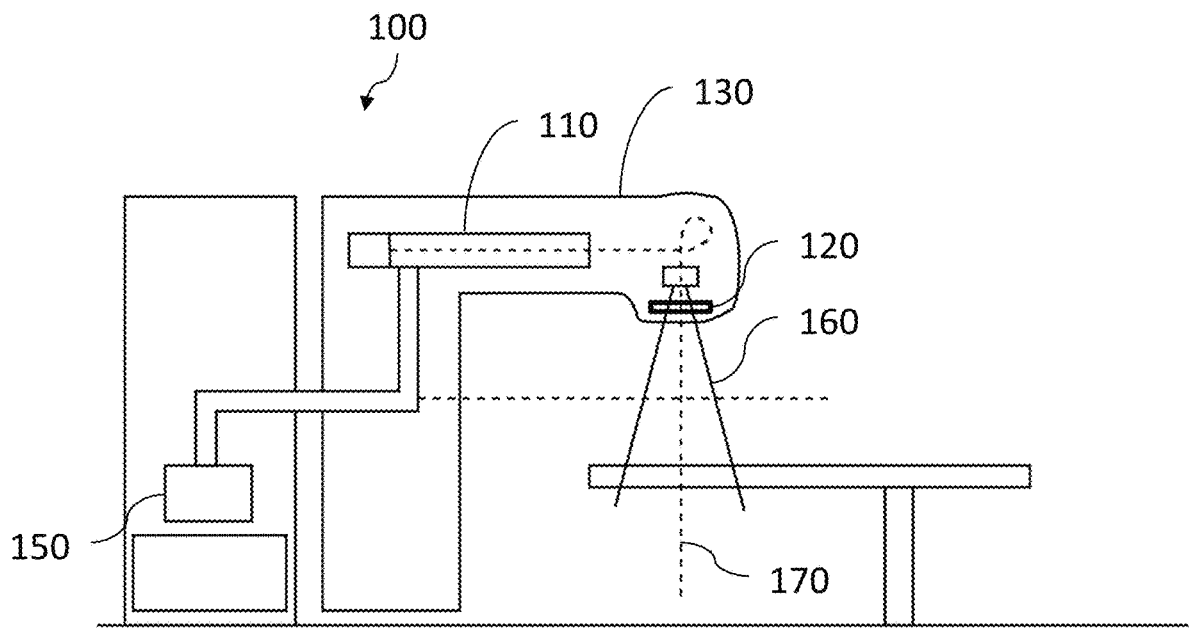
FIG. 1B is a diagram illustrating a side-sectional view of the simplified exemplary radiation delivery system of FIG. 1A in accordance with certain aspects of the present disclosure.

FIGS. 1A and 1B depict an exemplary radiation delivery system 100. This exemplary system is an open (or "C-arm") type system that includes a linear accelerator (e.g., element 110 in FIG. 1B) working with an RF source 150, a multileaf collimator 120, and a rotatable gantry 130. In this exemplary system, the linear accelerator and multileaf collimator are mounted within the rotatable gantry to allow radiation beam 160 to be delivered along beam axis 170 to a patient 10 at multiple angles. FIG. 1A also depicts an accessory tray 140 that can permit the mounting or positioning of hardware or devices between the radiation source and the patient. As described further herein, the technologies of the present disclosure can be used with radiation delivery systems such as the exemplary system depicted in FIGS. 1A and 1B, as well as with other types of radiotherapy systems.

Figure 2:
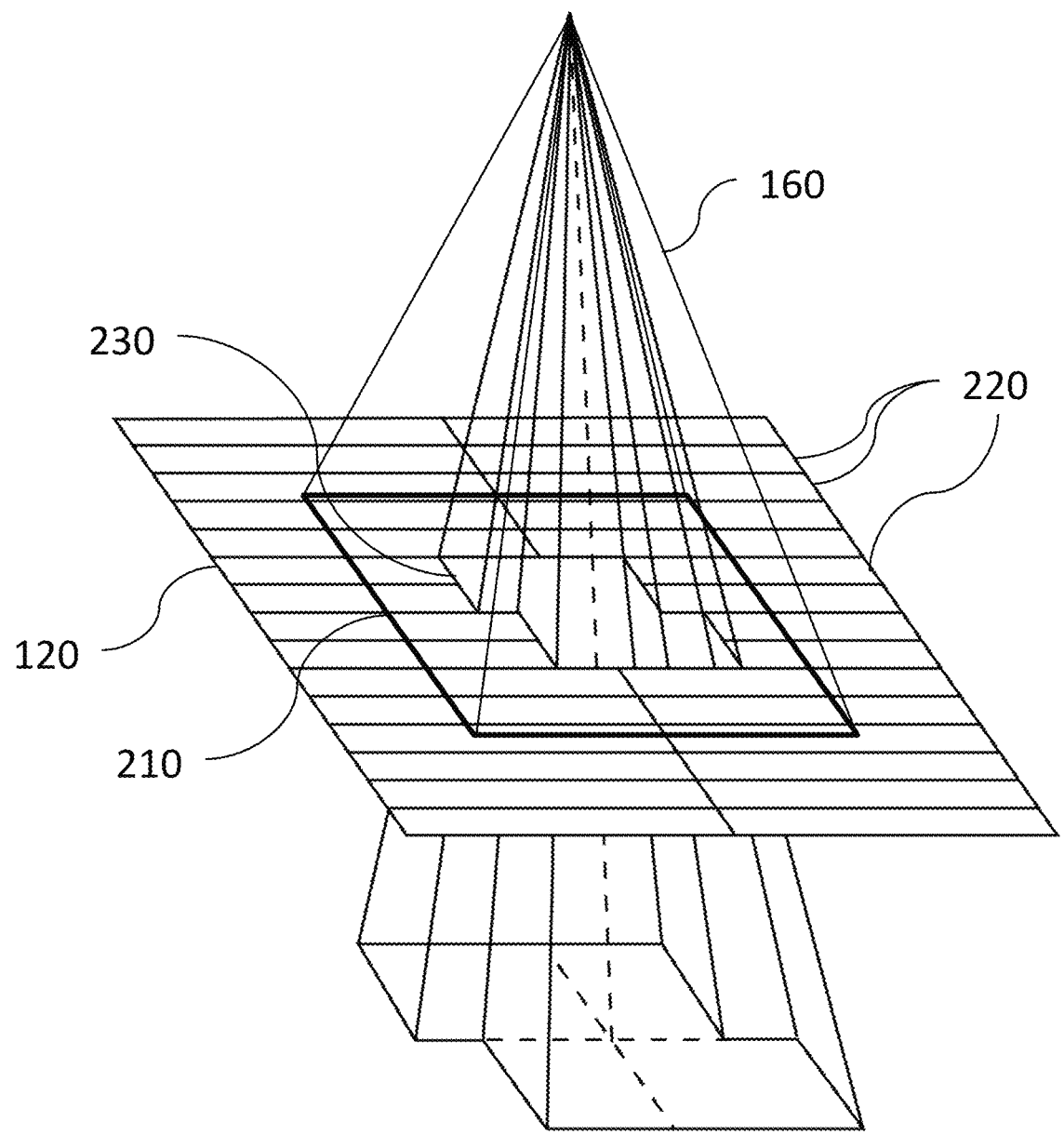
FIG. 2 is a diagram illustrating a perspective view of a simplified exemplary multileaf collimator shaping a radiation field in accordance with certain aspects of the present disclosure.

When performing radiation therapy quality assurance, one element of the radiation therapy device that can be assessed is the multileaf collimator (e.g., through verifying the collimator's leaf positions). One method for MLC configuration verification may involve examining the shape of the radiation field delivered to the patient by a radiation delivery system 100 including a radiation source (e.g., linear accelerator 110) configured to deliver a radiation beam 160. As shown in the simplified example of FIG. 2, a radiation field 210 can be shaped by blocking some portions with the leaves 220 of a multileaf collimator 120 to form an aperture 230. The portion of the radiation field that passes through the aperture will then proceed to the patient to deliver a dose of radiation in the desired shape. As used herein, the term "radiation field" can refer to radiation before or after being shaped by a collimator.

Scintillating materials may be used to determine the shape of a radiation field emerging from a multileaf collimator. "Determining the shape" can include determining the overall shape, determining particular MLC leaf positions (which provides information regarding the shape), etc.

"Scintillators," as discussed herein, are understood to include any material that, when hit by radiation, emit radiation (e.g., particle or photon) that can be detected (for example, by a camera). Scintillators include materials that absorb incoming radiation and then re-emit a portion of the absorbed energy in the form of light. It should be noted that when the term "light" is used herein, it is intended to include radiation within, or not within, the visible spectrum (for example, scintillators that emit infrared or other types of radiation are contemplated). Examples of scintillators can include plastic scintillators (such as Li6 plastic scintillators or polyethylene naphthalate), luminophores, crystal scintillators, phosphorescent materials, etc. As used herein, a "camera" can be any device that can detect radiation (e.g., light) coming from a scintillator. Examples of cameras can include CCD cameras, photodiodes, photomultiplier tubes, etc.

Figure 3:
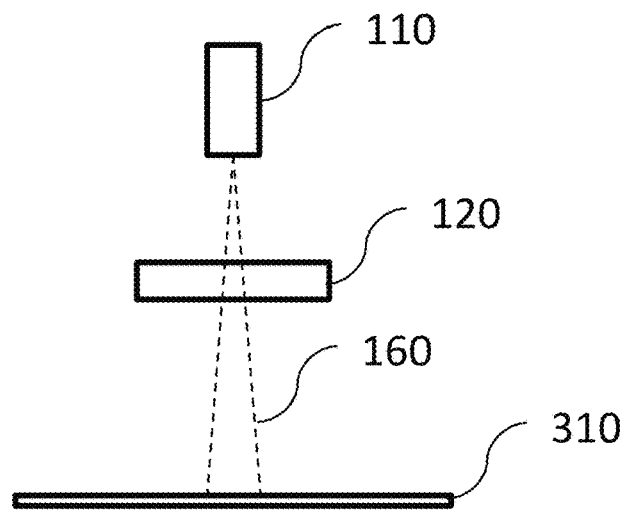
FIG. 3 is a diagram illustrating views of a simplified exemplary radiation pattern at a scintillator in accordance with certain aspects of the present disclosure.
Figure 3:
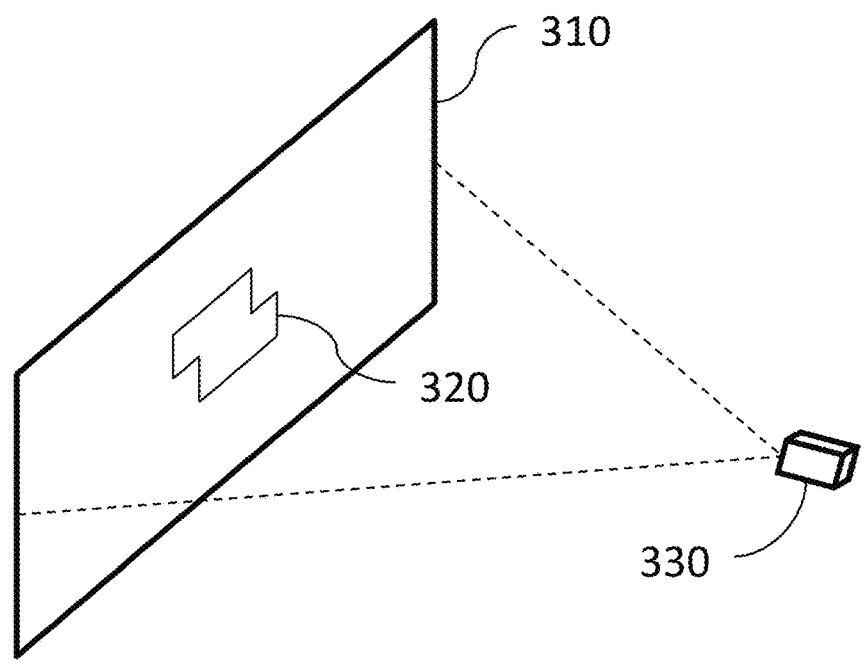

The top portion of FIG. 3 illustrates a simplified example of a scintillator 310 receiving a radiation beam 160 from radiation delivery system 110, after it passes through a multileaf collimator 120.

The lower portion of FIG. 3 illustrates a simplified example of a system for detecting a radiation pattern 320 from scintillator 310 using a camera 330. The radiation pattern 320 is related to the shape of the aperture formed by the multileaf collimator (as used herein, "radiation pattern" refers to the pattern present at the scintillator as it emits radiation/light after exposure to a radiation field).

Analysis of the images or signals acquired by the camera from the scintillator's radiation patterns can provide estimates of leaf positions of the multileaf collimator, independent of leaf position information that may be provided by the radiation delivery system itself.

The present disclosure describes, among other things, technologies utilizing scintillators to verify collimator leaf positions. However, contrary to what is common in the art, the present disclosure describes certain embodiments that utilize a scintillator that is tilted, so as to not be perpendicular to the axis of the radiation beam. Also contrary to the art, certain embodiments disclose a scintillator system with a very shallow angle between the camera and the scintillator. For example, disclosed systems may be configured such that the angle between a planar scintillator and the camera's line of sight is less than 10 degrees.

Figure 4:
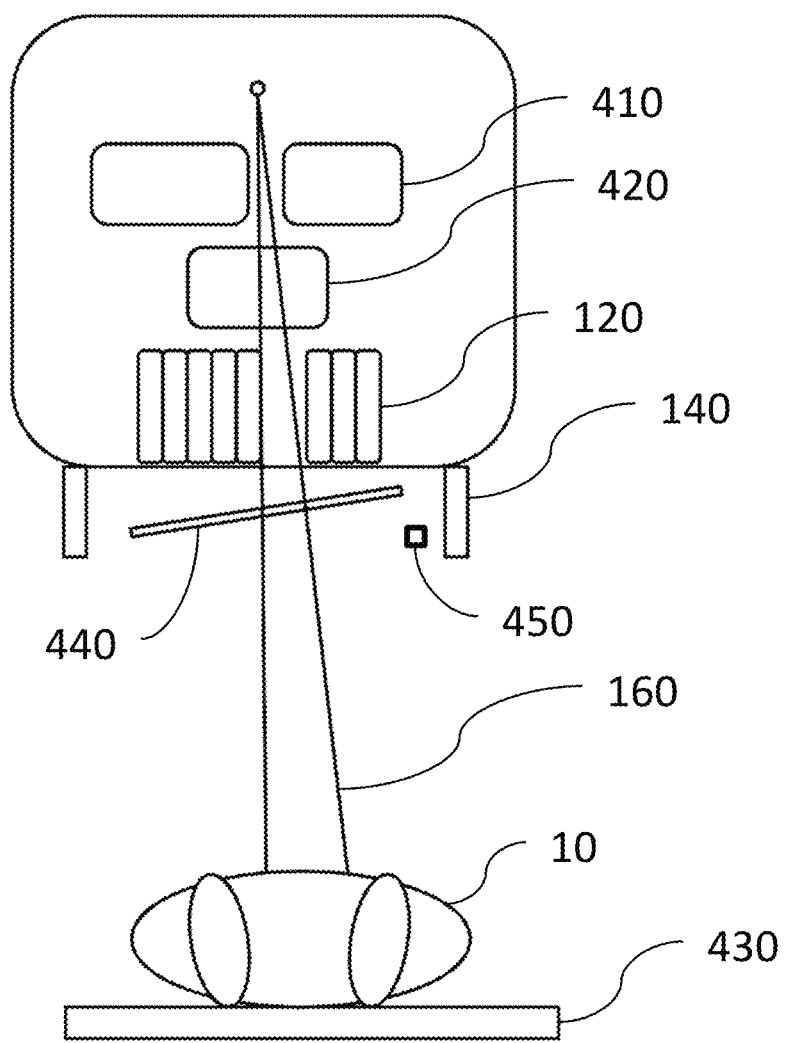
FIG. 4 is a diagram illustrating an end-perspective view of a simplified exemplary scintillator fixed in an orientation that is not perpendicular to the radiation beam axis in accordance with certain aspects of the present disclosure.

One implementation of the disclosed technology for determining at least a portion of a shape of a radiation field is depicted in FIG. 4. The figure illustrates a simplified representation of a radiation source 402 and a series of collimators (an X-axis jaw 410, a Y-axis jaw 420, and a multileaf collimator 120). Also illustrated is a patient 10 lying on a couch 430 such that the patient is hit by radiation beam 160 after its passes through the collimators. An accessory tray 140 is also depicted between the collimators and the patient couch.

The exemplary system of FIG. 4 can also include a scintillator 440 and a camera 450 configured to acquire images of light emitted by the scintillator during delivery of the radiation beam. As shown in FIG. 4, the scintillator and camera system can be configured to be located between the radiation source and a patient couch, thus functioning as an entrance detector.

It is contemplated that scintillator 440 may include a planar sheet of scintillating material or may include a curved sheet of scintillating material that may, for example, be oriented to have its convex surface facing toward the camera. In some embodiments, scintillator 440 may be sized to be large enough to cover the largest radiation field the radiation delivery system can deliver (at the location of the scintillator). In other embodiments, scintillator 440 may be more compact and may be smaller than the largest radiation field the system can deliver at the location of the scintillator, yet still sufficient for performing some measure of quality assurance.

Figure 5A:
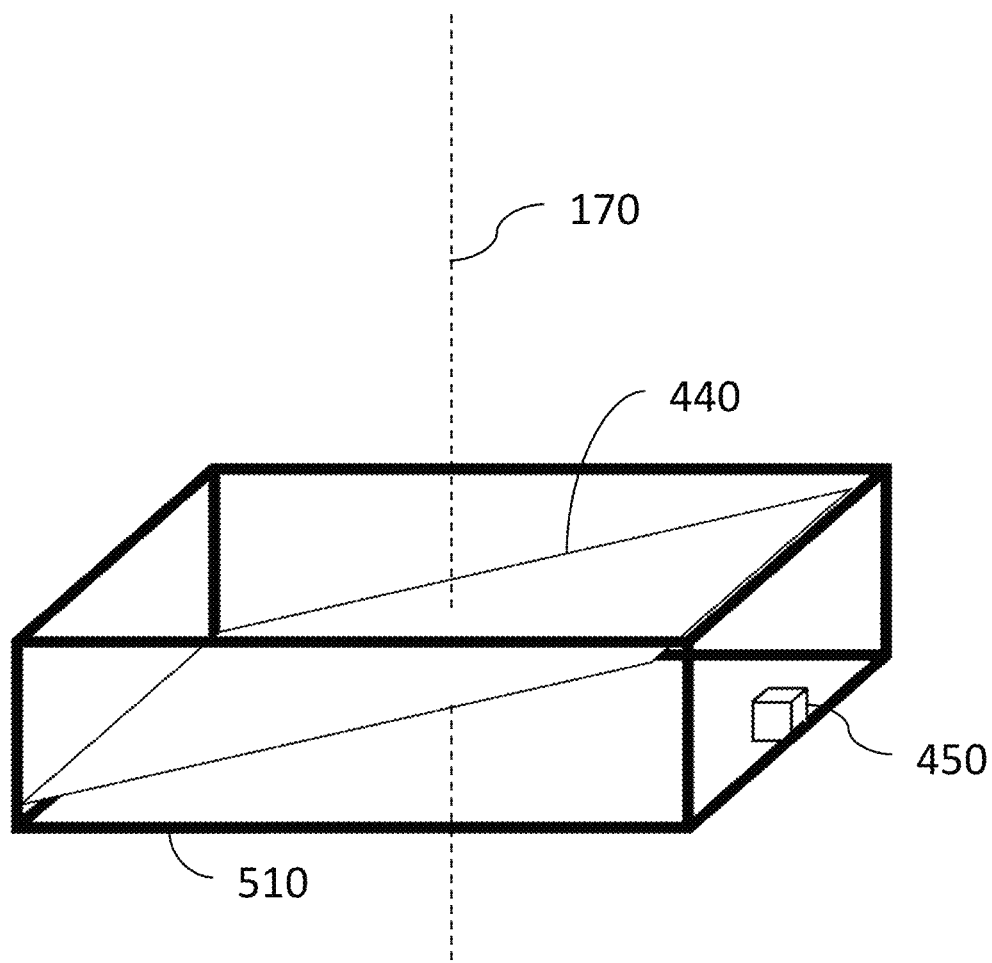
FIG. 5A is a diagram illustrating a perspective view of a simplified exemplary scintillator and camera fixed in a supporting structure in accordance with certain aspects of the present disclosure.

As illustrated in FIG. 5A, scintillator 440 and camera 450 can be fixed in a support structure 510. The support structure 510 may then be configured to be mounted to a radiation delivery system so that the scintillator will be struck by the radiation treatment beam.

The scintillator and camera are preferably fixed to the support structure in a manner that sets a specific desired geometric relationship between the scintillator and camera. The exemplary embodiment depicted in FIG. 5A illustrates a simplified framework where the scintillator is located within the support structure and the camera is located and configured to view one side of the scintillator (e.g., its bottom surface). It is contemplated, however, that the camera may be placed in a position to view the top surface of the scintillator or that more than one camera may be used.

In some embodiments, the scintillator and camera can be fixed to the support structure so that when the support structure is mounted to the radiation delivery system, the scintillator is not perpendicular to an axis of the radiation beam. FIG. 4 illustrates such an example of a scintillator 440 not being perpendicular to the axis 170 of radiation beam 160. When referring herein to a scintillator being oriented so that it is not perpendicular to an axis of the radiation beam, such refers to an orientation that is purposefully not perpendicular (i.e., as opposed to an orientation that may slightly deviate from an intended perpendicular positioning).

Some embodiments may have the scintillator fixed to the support structure so that the scintillator will be at an angle of between 80 to 89 degrees or between 91 and 110 degrees relative to the axis of the radiation beam when the support structure is mounted to the radiation delivery system. In other embodiments, the scintillator can be at an angle of between 84 and 88 degrees or between 92 and 96 degrees relative to the axis of the radiation beam when the support structure is mounted to the radiation delivery system. While the exemplary embodiment depicted in FIG. 4 shows a tilt in the Y direction, it is contemplated that a similar tilt could be implemented in the X direction or in both the X and Y directions.

In some embodiments, such as the one depicted in FIG. 5A, camera 450 and scintillator 440 can be fixed to support structure locations that maximize the angle between the camera and the scintillator. In such examples, the camera may be at one end of the support structure, as depicted, or may be in a corner of the support structure, or may even be located outside the perimeter of the support structure. Such embodiments can be beneficial in that the resolution of the radiation pattern imaged by the camera can be increased as compared to smaller angles where the radiation pattern is viewed more edge-on.

The design of the support structure can be substantially open above and/or below the scintillator to reduce or eliminate material that may attenuate the radiation therapy beam. Alternatively, the scintillator and the camera can be substantially enclosed by the support structure (for example, to prevent dust from accumulating on the scintillator or to protect it from damage or scratching). In such embodiments, the top portion and/or bottom portion of the support structure may be designed to provide only minimal attenuation of a radiation beam. For example, the top and/or bottom portion may be a layer of thin plastic or glass that causes only slight attenuation of the radiation beam.

The example depicted in FIG. 5A can represent a support structure 510 that substantially encloses the scintillator (i.e., is closed on all sides), but FIG. 5A is also intended to depict an example where the support structure 510 is merely a frame for mounting the scintillator and camera—with all the sides and the top/bottom being open.

Figure 5B:
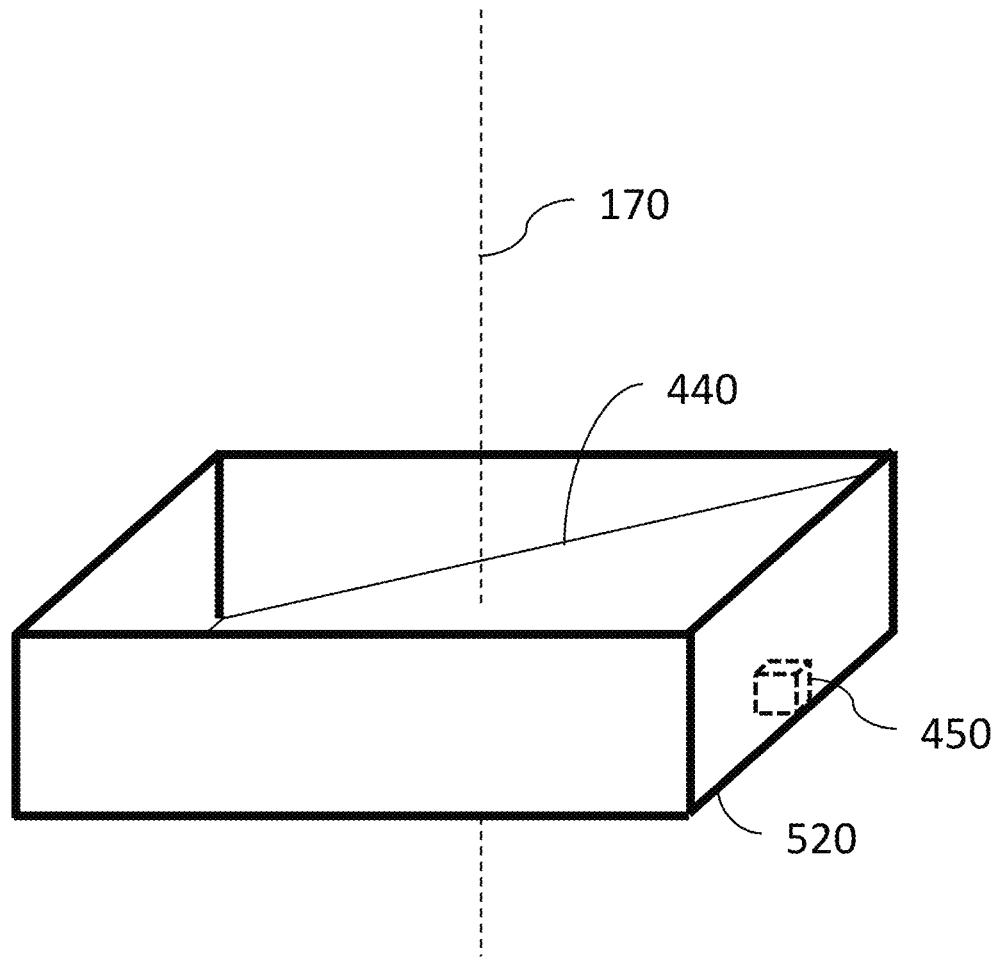
FIG. 5B is a diagram illustrating a perspective view of a simplified exemplary scintillator and camera fixed in a supporting structure that is open on a top and bottom portion in accordance with certain aspects of the present disclosure.

FIG. 5B Illustrates another exemplary embodiment in which the top portion and bottom portion of support structure 520 are open to allow light or other radiation unobstructed access to/through the scintillator, but where the support structure 520 also includes closed structural portions on its sides.

The present disclosure contemplates support structures that are constructed to include any combination of open or closed or transparent/translucent top, bottom or side materials.

Some embodiments of the present disclosure can enable the use of a visible light source (e.g., a tungsten or any sort of atomic lamp, or a white light source) to check the shape of a collimator aperture while the scintillator/support structure is in place. In such embodiments, the support structure can include translucent or transparent portions, which may be, for example, the top portion, bottom portion, or any portion(s) that form the sides of the support structure. It is contemplated that any combination of portions of the support structure may be translucent or transparent. Similarly, the scintillator may also be translucent or transparent. Such translucent or transparent support structure portions and/or scintillators can allow formation of a pattern at a target location (e.g., at the isoplane) corresponding to the shape of a collimator aperture when a light source shines light through the collimator aperture onto the scintillator and/or supporting structure portion. The present disclosure contemplates that any embodiments herein (not just planar scintillator embodiments) can incorporate transparent or translucent support structure portions and/or scintillators.

As used herein, the term "transparent" means that light corresponding to the shape of the collimator aperture is able to pass through without significant distortion, resulting in a pattern that can be accurately related to the shape of the collimator aperture. Similarly, as used herein, the term "translucent" means that light is able to pass, but there may be some distortion or dimming of the light and the resulting pattern corresponding to the shape of the collimator aperture. In embodiments where a translucent material is used, it is contemplated that degree of distortion will not be prohibitive of providing a pattern that can be utilized in radiation therapy quality assurance for determining the shape of a collimator aperture. Also, it is contemplated that the transparent or translucent material described herein can have any degree of attenuation of light. For example, a transparent scintillator may attenuate 50% of light but still allow a sharp (though dimmer) pattern to be formed at the target location. According to the type of application desired, translucent or transparent scintillators can have a polyvinyltoluene base, optionally including some fraction of lead (e.g., approximately 2%—appropriate for x-ray dosimetry), etc.

In some embodiments, the support structure can be configured to be mounted to the radiation delivery system at an accessory tray disposed between the radiation source and a patient couch. For example, a linear accelerator may have an accessory tray or slot into which the support structure may be mounted. It thus contemplated herein that when reference is made to a support structure being "configured to be mounted," this can include, for example, being configured in a way to be removably mounted (e.g., structurally designed to slide into an accessory tray slot or specifically sized to fit within the tray). Support structures herein are also contemplated to be configured to be mounted by virtue of more permanent structures such as the provision of screw holes or other fastening accessories to aid in mounting to a particular portion of a radiation delivery system.

In certain embodiments, the scintillator(s) and camera(s) can be fixed to the support structure in a manner so that the whole assembly fits entirely within an accessory tray. The support structure mounting, in conjunction with specific fixation therein of the scintillator and camera can result in a tilted scintillator orientation with regard to the axis of the radiation beam. For example, mounting the support structure into a linac accessory tray that is perpendicular to the axis of the radiation beam, when the scintillator is fixed at an angle within the supporting structure, results in the scintillator being tilted with regard to the axis of the radiation beam.

Figure 6:
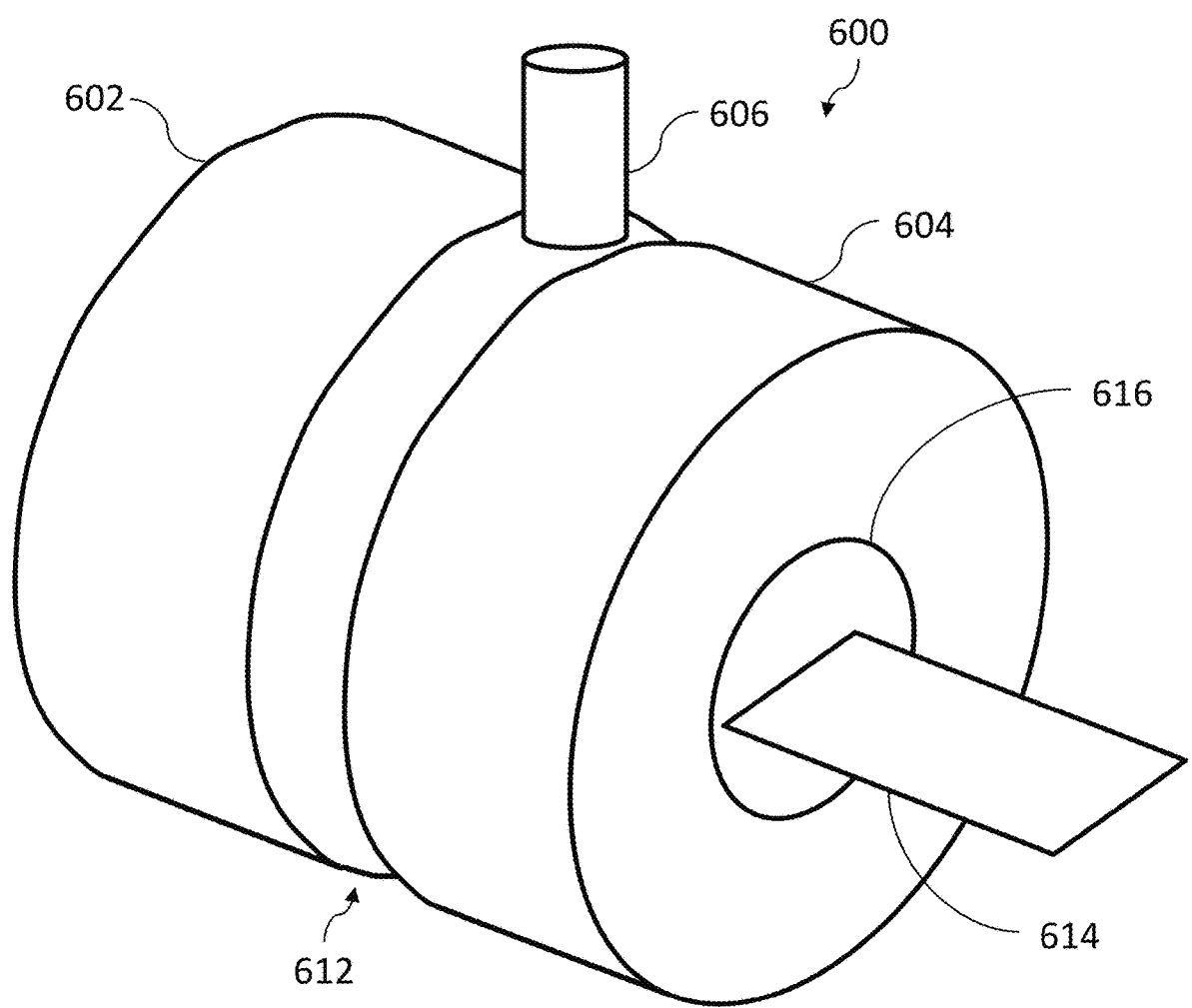
FIG. 6 is a diagram illustrating a perspective view of a simplified exemplary combined radiotherapy and medical imaging system in accordance with certain aspects of the present disclosure.

In contrast to the scintillator/camera systems described above for a C-arm type radiation delivery system, the present disclosure contemplates alternative embodiments for implementation with radiation delivery systems having a bore, for example, a radiation delivery system combined with an imaging system such as an MRI. FIG. 6 shows a simplified example of such a system 600 that includes first and second magnet housings 602 and 604 separated by gap region 612. A radiation source 606 can be mounted to a gantry adjacent to or in a gap region 612. A patient can be positioned on couch 614 inside bore 616 of the magnet so that the gantry can cause rotation of radiation source 606 around the patient.

Figure 7:
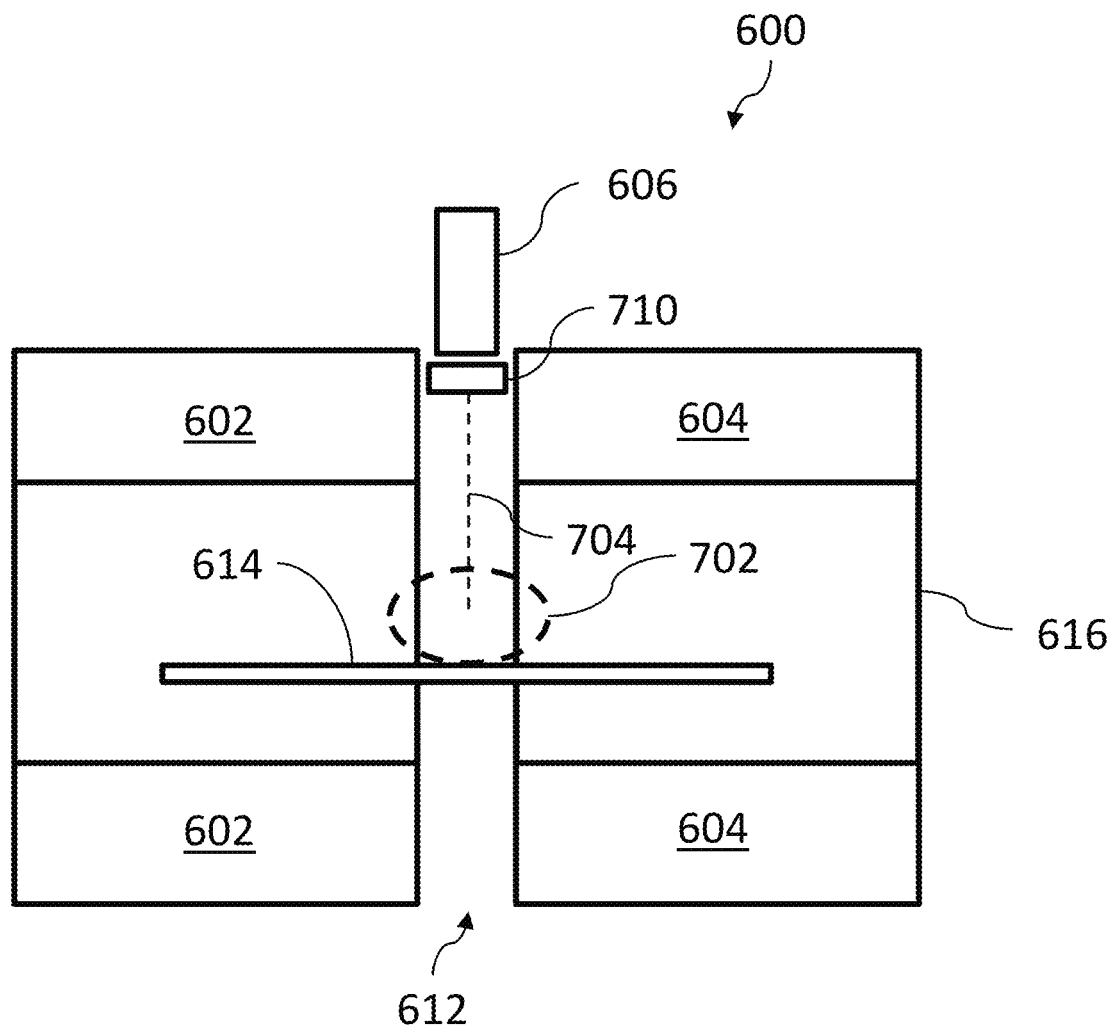
FIG. 7 is a diagram illustrating a side-sectional view of the simplified exemplary combined radiotherapy and medical imaging system of FIG. 6 in accordance with certain aspects of the present disclosure.

FIG. 7 depicts a cross-sectional view of the exemplary system shown in FIG. 6. Such a system can be used to image a target region 702 (e.g., a volume and/or area within a patient), while radiation source 606 emits radiation 704 for patient treatment. Also shown is a multileaf collimator 710 for shaping the radiation beam directed toward the patient. The system illustrated in FIGS. 6 and 7 is only one example of a radiotherapy system having a bore that is compatible with embodiments of the present disclosure. Implementations of the technologies herein may also be used with other types of radiotherapy systems that include a patient bore.

Scintillators that are shaped or configured for radiotherapy systems having a bore may be utilized in certain implementations. For example, as shown FIG. 8, scintillator 810 can be mounted to radiation delivery system 600 such that scintillator 810 substantially follows the contour of a bore 616 of a radiation delivery system 600. As noted above with regard to FIGS. 6 and 7, the bore may be part of an MRI-guided radiotherapy system. "Substantially following the contour of a bore" is understood to include, for example, following the internal surface of the bore or having generally the same contour as the bore but a slightly larger or smaller diameter, etc.

Figure 8:
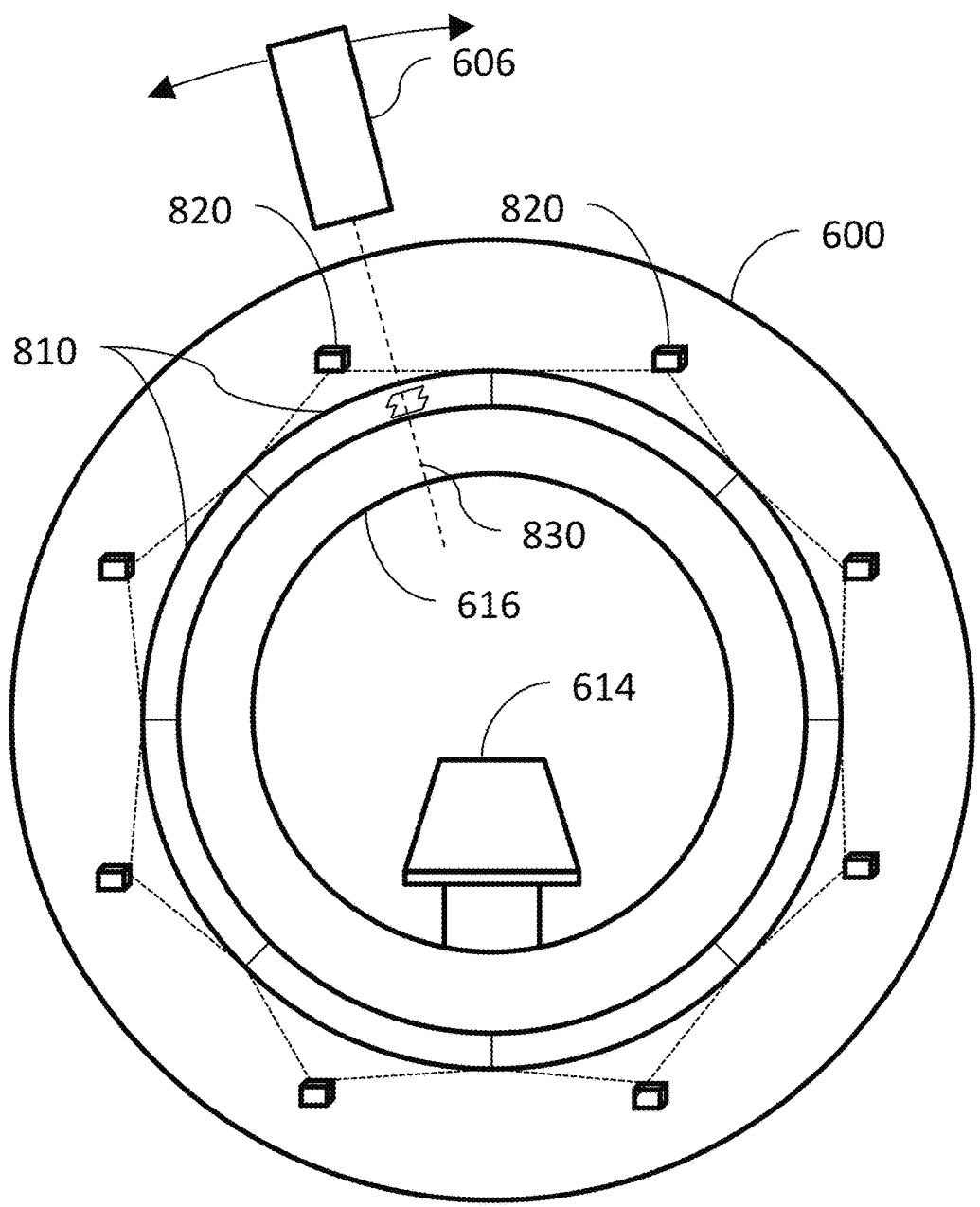
FIG. 8 is a diagram illustrating an end-perspective view down the bore of the simplified exemplary combined radiotherapy and medical imaging system of FIG. 6, showing exemplary scintillators and cameras in accordance with certain aspects of the present disclosure.

The scintillator may be a continuous sheet of scintillating material or may be comprised of multiple sheets. The example of FIG. 8 illustrates an exemplary scintillator having multiple curved sheets of scintillating material, specifically, eight curved sheets, each covering 45 degrees of the bore. In other implementations, the scintillator may be made up of a number of planar sheets of scintillating material. For example, the configuration shown in FIG. 8 could instead be comprised of eight planar sheets, meeting at their edges. It is contemplated that any number of curved or planar sheets can be implemented, in any feasible combination, to cover a desired portion of the bore and they can be located at any radial distance from the axis of the bore.

While the scintillator can extend around the entire circumference of the bore, it is not essential that it do so. For example, the scintillator can cover any degree or angular measure of the bore (e.g., 270 degrees, 180 degrees, 90 degrees, 45 degrees, etc.) and may be constituted of any number of sheets (e.g., ten sheets covering 27 degrees each, 18 sheets covering 10 degrees each, etc.).

As described in further detail herein, mounting the scintillator to the radiation delivery system may include, for example: mounting the scintillator directly to a portion of the radiation delivery system such as the gantry, the linac, the MLC, etc.; mounting the scintillator to the bore of an imaging system associated with the radiation delivery system (e.g., an MRI for an MRI-guided radiation therapy system); and, mounting the scintillator indirectly, for example, mounting the scintillator to a supporting structure that can in turn be mounted to portions of the overall system (e.g., RT device, MRI, etc.).

In some embodiments, the scintillator can be mounted so it is at an angle to the radiation beam or the scintillator can be mounted so that at least one portion of the scintillator remains perpendicular to axis 830 of the radiation beam when the radiation source 606 is controlled to move around the bore. For example, in instances where the radiation beam axis 830 is radial and the scintillator is curved to be concentric with the bore, at least one portion of the scintillator (e.g., where axis 830 intersects the scintillator) would be perpendicular to axis 830.

One or more cameras 820 configured to acquire images of light emitted by the scintillator during delivery of the radiation beam can be utilized. Similar to the previously-described embodiments, these may be mounted so as to have a shallow angle between the scintillator and the camera. For example, the cameras 820 can be configured to be mounted at an angle of greater than 0 and less than 10 degrees relative to the scintillator. In other embodiments, the cameras may be mounted to result in angles of 10-20, 20-30, 30-40, 40-50 or 50-60 degrees between the scintillator and the line of sight of the camera.

Cameras 820 can be placed on the bore at various locations so they are able to view at least a portion of the scintillator. The cameras can be small so as to provide minimal intrusion into the inner volume of the bore where the patient is located. As shown in the example of FIG. 8, each of the scintillator sections or sheets may have a corresponding camera 820 with a field of view covering it (shown approximately by the dotted lines). The number and disposition of the cameras 820 and their fields of view in FIG. 8 are examples only and other configurations are contemplated. For example, the fields of view can cover only a portion of a section rather than an entire section, the cameras 820 can be located at any axial location along the bore, and they can be on either side of the scintillator.

In some embodiments, a support structure can be configured to be mounted to the bore, and the one or more cameras can be fixed to the support structure. In the present example, a support structure configured to be mounted to the bore may include a cylindrical framework that generally conforms to the shape of the bore, such that the supporting structure having the cameras can be inserted or installed in the bore, without the need to mount individual cameras to the bore structure itself. In such embodiments, and other embodiments, such as those described above with reference to FIG. 8, the cameras 820 can be oriented to view respective portions of the scintillator adjacent to the cameras. Here, the scintillator "adjacent the camera" means the scintillator can be located at least partially at the same angular location as the camera. In addition to mounting cameras on such a support structure, other embodiments can include having the scintillator also mounted to the support structure. Such embodiments can allow for the entire assembly of scintillators and cameras to be inserted or mounted to the bore as a unit, rather than as individual components.

Methods and software that enable the determination of MLC leaf positions are disclosed herein. Leaf positions can be reflected in scintillator radiation patterns imaged by one or more cameras, as described above. In one embodiment, leaf position determination can be facilitated by analyzing the edges of radiation patterns. As used herein, "radiation pattern" means the image of (or data representing the image of) scintillator light emitted due to interaction between the scintillator and a radiation beam.

Figure 9:
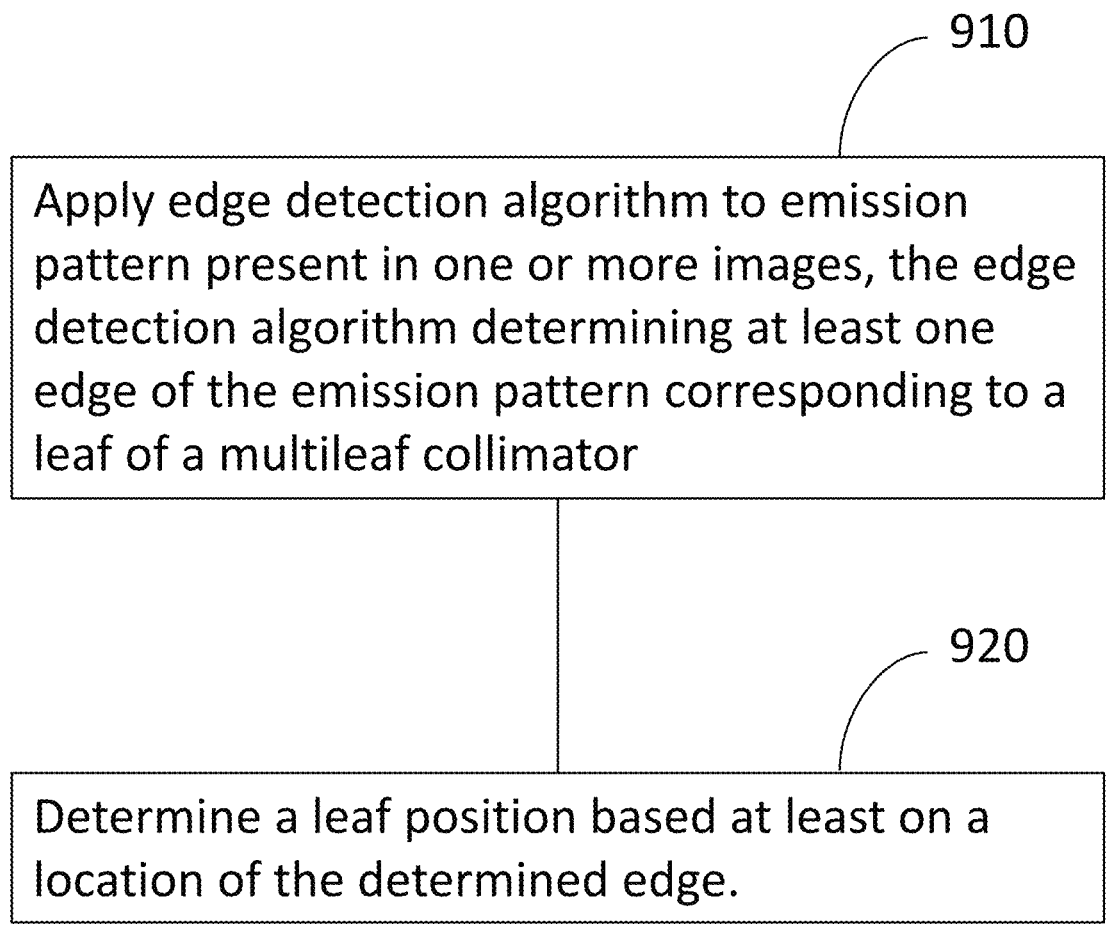
FIG. 9 is a diagram illustrating an exemplary method of determining leaf positions of a multileaf collimator in accordance with certain aspects of the present disclosure.

As illustrated by the example in FIG. 9, computer software can perform operations to determine edges of a radiation pattern. For example, at 910, using the image data acquired from the camera(s), an edge detection algorithm (e.g., a Canny edge detection algorithm) can be applied to a radiation pattern present in the images. The edge detection algorithm can determine at least one edge of the radiation pattern corresponding to a leaf of a multi-leaf collimator. From this, at 1020, a leaf position can be determined based at least on a location of the determined edge. Following this determination, it is possible to compare leaf positions during delivery of the radiation beam with planned leaf positions (e.g., as dictated by a radiation therapy plan and/or detailed in system log files). The comparison can thus be utilized in radiation therapy quality assurance.

The process of determining leaf positions can then include, for example, compensating for image distortion caused by (or inherently present in) a given camera or camera system. For example, lens aberrations, and camera placement with respect to the scintillator can be accounted for. One method of accounting for optical effects from the camera system can include performing a calibration procedure with a well-known pattern that allows for a mapping of points in the image acquired by the camera to real positions in the object plane (e.g., the plane of a planar scintillator sheet). This correction/mapping can be performed for any number of opposing leaves of the MLC.

As part of radiation therapy quality assurance, it can be desired to determine leaf positions at a plane through the isocenter. One method for doing so can include determining the effective size of an opening between collimator leaves at a plane parallel to the isocenter plane. Then, the effective MLC leaf positions at the isocenter plane can be determined based on the effective size, when geometrically extended to the isocenter plane.

Figure 10:
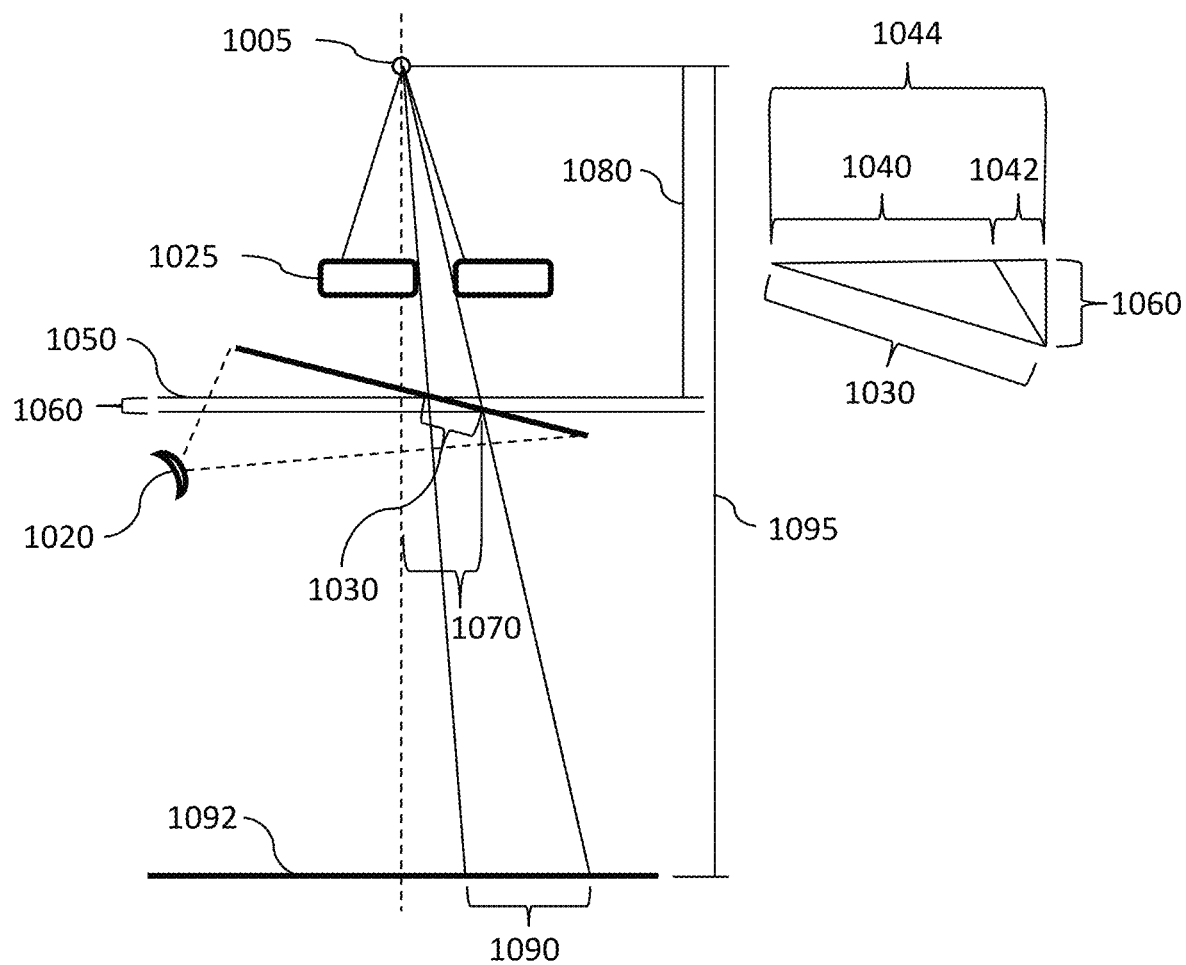
FIG. 10 is a diagram illustrating an exemplary geometric method of determining a leaf position of a multileaf collimator from a radiation pattern in accordance with certain aspects of the present disclosure.

An exemplary arrangement of a simplified system used for the above determination is illustrated in FIG. 10. Here, an example of a tilted scintillator 1010 is shown with a camera 1020 imaging the scintillator 1010. The radiation from radiation source 1005 passing through the MLC 1025 results in a radiation pattern at the scintillator. The shape of the radiation pattern is a length (length$_{screen}$) 1030 that corresponds to the size of the opening between MLC leaves (which can be directly related to the position of the MLC leaves). One exemplary formula for determining the length (length$_{pp}$) 1040 at on a plane parallel 1050 to the isocenter plane 1092 can be expressed as shown in Eq. 1, below.

$$length_{pp} = \sqrt{length_{screen}^2 - height^2} + \frac{x}{(d_1 + height)} \quad (1)$$

$$length_{pp} = \sqrt{length_{screen}^2 - height^2} + height \frac{x}{(d_1 + height)}.$$

In Eq. 1, the height is the height 1060 of the radiation pattern as measured in the vertical direction (or parallel to the beam axis). X is the X-coordinate 1070 of the right edge of the radiation pattern. d1 (element 1080) is the height from the radiation source to the plane parallel to the isocenter plane. The expanded view on the right side of FIG. 10 illustrates that length$_{pp}$ 1040 can be found by accounting for the vertical projection 1042 of the radiation pattern to the plane parallel 1050. Once length$_{pp}$ is found the length (length$_{iso}$) 1090 at the isocenter plane 1092 can be determined according to the following relation:

$$length_{iso} = \frac{d_2}{d_1} length_{pp}. \qquad (2)$$

In Eq. 2, d$_2$ (element 1095) is the distance from the radiation source to the isocenter plane 1092. The above description and solution of the simplified geometrical arrangement of the scintillator and camera system should not be considered limiting or exclusive of other solutions that may be implemented for embodiments described herein.

The methods and operations described herein can further enable the determination of fluence maps at the isocenter plane, which can be useful for performing radiation therapy quality assurance. For example, the present disclosure contemplates software that can perform operations that include calculating a fluence map based at least on the leaf positions determined using the scintillator and also on beam output data obtained from the radiation therapy system. Furthermore, operations such as calculating a dose at a target location based at least on the fluence map and a patient image obtained from an imaging system may also be performed.

In the following, further features, characteristics, and exemplary technical solutions of the present disclosure will be described in terms of items that may be optionally claimed in any combination:

Item 1: A system for determining at least a portion of a shape of a radiation field generated by a radiation delivery system that includes a radiation source configured to deliver a radiation beam, the system comprising: a scintillator; a camera configured to acquire images of light emitted by the scintillator during delivery of the radiation beam; and a support structure configured to be mounted to the radiation delivery system, the scintillator and the camera fixed to the support structure such that when the support structure is mounted to the radiation delivery system, the scintillator is not perpendicular to an axis of the radiation beam.

Item 2: The system of any one of the preceding items, wherein the system is configured to be located between the radiation source and a patient couch.

Item 3: The system of any one of the preceding items, wherein the scintillator includes a planar sheet of scintillating material.

Item 4: The system of any one of the preceding items, wherein the scintillator includes a curved sheet of scintillating material and the curved sheet is oriented to have its convex surface oriented so as to be facing toward the camera.

Item 5: The system of any one of the preceding items, wherein the scintillator has a size large enough to cover the largest radiation field that the radiation delivery system can deliver at the location of the scintillator.

Item 6: The system of any one of the preceding items, wherein the scintillator is transparent, the scintillator allowing formation of a pattern at a target location corresponding to the shape of a collimator aperture when a light source shines light through the collimator aperture onto the scintillator.

Item 7: The system of any one of the preceding items, wherein the scintillator and the camera are fixed to the support structure in a manner that sets a specific desired geometric relationship between the scintillator and the camera.

Item 8: The system of any one of the preceding items, wherein the scintillator is fixed to the support structure so that the scintillator will be at an angle of between 80 to 89 degrees or between 91 and 110 degrees relative to the axis of the radiation beam when the support structure is mounted to the radiation delivery system.

Item 9: The system of any one of the preceding items, wherein the scintillator is fixed to the support structure so that the scintillator will be at an angle of between 84 and 88 degrees or between 92 and 96 degrees relative to the axis of the radiation beam when the support structure is mounted to the radiation delivery system.

Item 10: The system of any one of the preceding items, wherein the camera and the scintillator are fixed to the support structure locations that maximize the angle between the camera and the scintillator.

Item 11: The system of any one of the preceding items, wherein the support structure is configured to allow mounting in an accessory tray disposed between the radiation source and a patient couch.

Item 12: The system of any one of the preceding items, wherein the support structure has a top portion and a bottom portion that is open.

Item 13: The system of any one of the preceding items, wherein the scintillator and the camera are substantially enclosed by the support structure, and the support structure includes a top portion and a bottom portion that provide only minimal attenuation of the radiation beam.

Item 14: A system for determining at least a portion of the shape of a radiation field generated by a radiation delivery system that includes a radiation source configured to deliver a radiation beam, system comprising: a scintillator mounted to the radiation delivery system such that the scintillator substantially follows a contour of a bore of the radiation delivery system; and one or more cameras configured to acquire images of light emitted by the scintillator during delivery of the radiation beam, the one or more cameras configured to be mounted an angle of greater than 0 and less than 10 degrees relative to the scintillator.

Item 15: The system of any one of the preceding items, wherein the scintillator is a curved sheet of scintillating material.

Item 16: The system of any one of the preceding items, wherein the scintillator comprises a plurality of planar sheets of scintillating material.

Item 17: The system of any one of the preceding items, wherein at least one portion of the scintillator remains perpendicular to the axis of the radiation beam when the radiation source is controlled to move around the bore.

Item 18: The system of any one of the preceding items, wherein the bore is part of an MRI-guided radiotherapy system.

Item 19: The system of any one of the preceding items, further comprising a support structure configured to be mounted to the bore, and the one or more cameras are fixed to the support structure.

Item 20: The system of any one of the preceding items, wherein the one or more cameras are oriented to view respective portions of the scintillator adjacent to the one or more of cameras.

Item 21: The system of any one of the preceding items, wherein the scintillator is also mounted to the support structure.

Item 22: The system of any one of the preceding items, further comprising a non-transitory, machine-readable medium storing instructions which, when executed by at least one programmable processor, cause operations comprising: applying an edge detection algorithm to a radiation pattern present in the images, the edge detection algorithm determining at least one edge of the radiation pattern corresponding to a leaf of a multi-leaf collimator; and determining a leaf position based at least on a location of the determined edge.

Item 23: The system of any one of the preceding items, the operations further comprising comparing the leaf position during delivery of the radiation beam with a planned leaf position, the comparing utilized in radiation therapy quality assurance.

Item 24: The system of any one of the preceding items, the operations further comprising calculating a fluence map based at least on the leaf position and beam output data obtained from the radiation therapy system.

Item 25: The system of any one of the preceding items, the operations further comprising calculating a dose at a target location based at least on the fluence map and a patient image obtained from an imaging system.

Item 26: The system of any one of the preceding items, wherein the dose is a three-dimensional dose delivered at the target location.

Item 27: A system or computer program product of any of the preceding items, comprising a non-transitory, machine-readable medium storing instructions which, when executed by at least one programmable processor, cause the at least one programmable processor to perform operations comprising: controlling a camera to acquire images of light emitted by a scintillator during delivery of a radiation beam, the scintillator and the camera fixed to a support structure such that when the support structure is mounted to a radiation delivery system, that the scintillator is not perpendicular to an axis of the radiation beam, the images capturing at least a portion of a shape of a radiation field generated by the radiation delivery system that includes a radiation source configured to deliver the radiation beam.

Item 28: The system or computer program product of any one of the preceding items, the operations further comprising: applying an edge detection algorithm to a radiation pattern present in the images, the edge detection algorithm determining at least one edge of the radiation pattern corresponding to a leaf of a multi-leaf collimator; and determining a leaf position based at least on a location of the determined edge.

Item 29: The system or computer program product of any one of the preceding items, the operations further comprising comparing the leaf position during delivery of the radiation beam with a planned leaf position, the comparing utilized in radiation therapy quality assurance.

Item 30: The system or computer program product of any one of the preceding items, the operations further comprising calculating a fluence map based at least on the leaf position and beam output data obtained from the radiation therapy system.

Item 31: The system or computer program product of any one of the preceding items, the operations further comprising calculating a dose at a target location based at least on the fluence map and a patient image obtained from an imaging system.

Item 32: The system or computer program product of any one of the preceding items, wherein the dose is a three-dimensional dose delivered at the target location.

The present disclosure contemplates that the calculations disclosed in the embodiments herein may be performed in a number of ways, applying the same concepts taught herein, and that such calculations are equivalent to the embodiments disclosed.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. A system for determining at least a portion of the shape of a radiation field generated by a radiation delivery system that includes a radiation source configured to deliver a radiation beam, system comprising:
    a scintillator mounted to the radiation delivery system such that the scintillator substantially follows a contour of a bore of the radiation delivery system; and
    one or more cameras configured to acquire images of light emitted by the scintillator during delivery of the radiation beam.

2. The system of claim 1, wherein the scintillator is a curved sheet of scintillating material.

3. The system of claim 1, wherein the scintillator comprises a plurality of planar sheets of scintillating material.

4. The system of claim 1, wherein at least one portion of the scintillator remains perpendicular to the axis of the radiation beam when the radiation source is controlled to move around the bore.

5. The system of claim 1, wherein the scintillator is at a larger radial distance than an internal surface of the bore.

6. The system of claim 1, wherein the scintillator is at a smaller radial distance than an internal surface of the bore.

7. The system of claim 1, wherein the bore is part of an MRI-guided radiotherapy system.

8. The system of claim 1, wherein the one or more cameras are configured to be mounted at an angle of greater than 0 and less than 10 degrees relative to the scintillator.

9. The system of claim 1, further comprising a support configured to be mounted to the bore, and the one or more cameras are fixed to the support.

10. The system of claim 9, wherein the one or more cameras are oriented to view respective portions of the scintillator adjacent to the one or more cameras.

11. The system of claim 9, wherein the scintillator is also mounted to the support.

12. The system of claim 1, further comprising a non-transitory, machine-readable medium storing instructions which, when executed by at least one programmable processor, cause operations comprising:
    applying an edge detection algorithm to a radiation pattern present in the images, the edge detection algorithm determining at least one edge of the radiation pattern corresponding to a leaf of a multi-leaf collimator; and
    determining a leaf position based at least on a location of the determined edge.

13. The system of claim 12, the operations further comprising comparing the leaf position during delivery of the radiation beam with a planned leaf position, the comparing utilized in radiation therapy quality assurance.

14. The system of claim 12, the operations further comprising calculating a fluence map based at least on the leaf position and beam output data obtained from the radiation therapy system.

15. The system of claim 14, the operations further comprising calculating a dose at a target location based at least on the fluence map and a patient image obtained from an imaging system.

16. A computer program product comprising a non-transitory, machine-readable medium storing instructions which, when executed by at least one programmable processor, cause the at least one programmable processor to perform operations comprising:
    controlling one or more cameras to acquire images of light emitted by a scintillator during delivery of a radiation beam, the scintillator mounted to a radiation delivery system such that the scintillator substantially follows a contour of a bore of the radiation delivery system.

17. The computer program product of claim 16, the operations further comprising:
applying an edge detection algorithm to a radiation pattern present in the images, the edge detection algorithm determining at least one edge of the radiation pattern corresponding to a leaf of a multi-leaf collimator; and
determining a leaf position based at least on a location of the determined edge.

18. The computer program product of claim 17, the operations further comprising comparing the leaf position during delivery of the radiation beam with a planned leaf position, the comparing utilized in radiation therapy quality assurance.

19. The computer program product of claim 18, the operations further comprising calculating a fluence map based at least on the leaf position and beam output data obtained from the radiation therapy system.

20. The computer program product of claim 16, the operations further comprising calculating a dose at a target location based at least on the fluence map and a patient image obtained from an imaging system.

21. The computer program product of claim 16, wherein the images are acquired with the one or more cameras which are mounted at an angle of greater than 0 and less than 10 degrees relative to the scintillator.

* * * * *